US009291600B2

(12) United States Patent
Bargatin et al.

(10) Patent No.: US 9,291,600 B2
(45) Date of Patent: Mar. 22, 2016

(54) PIEZORESISTIVE NEMS ARRAY NETWORK

(71) Applicant: CALIFORNIA INSTITUTE OF TECHNOLOGY, Pasadena, CA (US)

(72) Inventors: Igor Bargatin, Pasadena, CA (US); John Sequoyah Aldridge, Alhambra, CA (US); Edward Myers, Pasadena, CA (US); Michael L. Roukes, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 328 days.

(21) Appl. No.: 13/750,897

(22) Filed: Jan. 25, 2013

(65) Prior Publication Data

US 2014/0182361 A1  Jul. 3, 2014

Related U.S. Application Data

(60) Provisional application No. 61/748,340, filed on Jan. 2, 2013.

(51) Int. Cl.
  *G01H 1/00* (2006.01)
  *G01N 29/036* (2006.01)
  (Continued)

(52) U.S. Cl.
  CPC ............ *G01N 29/036* (2013.01); *G01N 29/022* (2013.01); *G01N 29/34* (2013.01); *G01N 2291/0256* (2013.01); *G01N 2291/0427* (2013.01)

(58) Field of Classification Search
  CPC ................ G01N 29/022; G01N 29/34; G01N 2291/0256; G01N 2291/0427

USPC .............. 73/579, 61.79; 331/65, 74, 154, 156
See application file for complete search history.

(56) References Cited

U.S. PATENT DOCUMENTS

| 4,596,697 A | * | 6/1986 | Ballato | ................ G01N 29/036 331/161 |
| 5,744,902 A | * | 4/1998 | Vig | .......................... G01G 3/16 310/360 |
| 6,722,200 B2 | * | 4/2004 | Roukes | .................... G01G 3/16 73/32 A |

(Continued)

FOREIGN PATENT DOCUMENTS

WO   WO 2011/006885   1/2011

OTHER PUBLICATIONS

Arlett, J. et al., "Comparative advantages of mechanical biosensors", *Nat. Nanotechnol.* 6, 203-15, (2011).

(Continued)

*Primary Examiner* — Laura Martin
*Assistant Examiner* — Samir M Shah
(74) *Attorney, Agent, or Firm* — The Marbury Law Group, PLLC

(57) ABSTRACT

A sensor for detecting analytes, a method of making the sensor, and a method of using the sensor. In one embodiment, the present invention comprises at least one array comprising a plurality of resonators. The resonators can be arranged in a plurality of rows and a plurality of columns, and can be connected in a combined series-parallel configuration. The resonators can be adapted to vibrate independently at about the same resonance frequency and about the same phase. The sensor can also comprise an actuator and a signal detector electrically coupled to the array. The sensor can also further comprise an analyte delivery system and can be functionalized for detection of at least one analyte.

97 Claims, 16 Drawing Sheets

(51) Int. Cl.
*G01N 29/02* (2006.01)
*G01N 29/34* (2006.01)

(56) References Cited

U.S. PATENT DOCUMENTS

| | | | | |
|---|---|---|---|---|
| 7,408,147 B2* | 8/2008 | Blick | B82Y 15/00 250/251 |
| 7,884,324 B2* | 2/2011 | Blick | H01J 1/32 250/306 |
| 7,990,336 B2* | 8/2011 | Maines | H01J 25/00 343/742 |
| 8,274,059 B2* | 9/2012 | Blick | H01L 49/025 250/397 |
| 8,384,042 B2* | 2/2013 | Gorrell | H01J 25/00 250/396 R |
| 8,441,635 B2* | 5/2013 | Schubert | G01N 15/02 256/335 |
| 8,507,785 B2* | 8/2013 | Layton | G02B 5/008 136/244 |
| 8,507,845 B2* | 8/2013 | Blick | H01J 43/246 250/281 |
| 8,530,831 B1* | 9/2013 | Coon | G01N 33/6848 250/281 |
| 8,610,989 B2* | 12/2013 | Avouris | B82Y 20/00 257/428 |
| 8,742,333 B2* | 6/2014 | Coon | H01J 49/10 250/282 |
| 8,988,061 B2* | 3/2015 | Datskos | G01R 29/0878 324/96 |
| 2002/0142477 A1* | 10/2002 | Lewis | G01N 33/0031 436/151 |
| 2002/0166962 A1* | 11/2002 | Roukes | G01N 33/54373 250/306 |
| 2007/0023621 A1* | 2/2007 | Blick | B82Y 15/00 250/251 |
| 2007/0029477 A1* | 2/2007 | Miller | G01N 27/624 250/290 |

OTHER PUBLICATIONS

Bargatin, I. et al., "Efficient electrothermal actuation of multiple modes of high-frequency nanoelectromechanical resonators", *Appl. Phys. Lett.* 90, 093116 (2007).

Bargatin, I. et al, "Large Scale Integration of Nanoelectromechanical Systems for Gas Sensing Applications", Nano Letters, 12, 1269-1274 (2012).

Jensen K. et al., "An atomic-resolution nanomechanical mass sensor", *Nat. Nanotechnol.*, 3, 533-537 (2008).

Guirardel, M. et al., "On-chip self-sensing function of a 4×4 matrix micromachined resonating piezoelectroc membranes for mass detection applications", IEEE International Ultrasonics, Ferroelectrics and Frequesncy Control Joint 50th Anniv. Conf. (2004).

Lee H. J. et al., "Highly Sensitive Detection of DMMP Using a CMUT-based Chemical Sensor", *Proc. IEEE Sensors Conf.*, 2122-2126 (2010).

LeHaye, M.D. et al. "Approaching the Quantum Limit of a Nanomechanical Resonator", *Science*, 304, 74-77 (2004).

Li et al., "Ultra-sensitive NEMS-based cantilevers for sensing, scanned probe and very high-frequency applications", *Nat. Nanotechnol.*, 2, 114-120 (2007).

Li et al., "Nanoelectromechanical Resonator Arrays for Ultrafast, Gas-Phase Chormatographic Chemical Analysis", *Nano Lett.* 10, 3899-3903 (2010).

Li et al., "Bottom-up assembly of large-area nanowire resonator arrays", *Nat. Nanotechnol.*, 3, 88-92 (2008).

Li et al., Disk-array design for suppression of unwanted modes in micromechanical composite-array filters, *Tech. Digest, 19th IEEE Int. Conf. on MicroElectroMechanical Systems (MEMS'06)*, Istanbul, Turkey, Jan. 22-26, 2006.

Li et al., "An MSI micromechanical differential disk-array filter", *Digest of Tech. Papers, 14th Int. Conf. on Solid-State Sensors & Actuators (Transducers'07)*, Lyon, France, Jun. 11-14, 2007.

Masmanidis et al., "Multifunctional Nanomechanical Systems Via Tunably Coupled Piezoelectric Actuation", *Science* 317, 780-783 (2007).

Naik, A.K. et al., "Towards single-molecule nanomechanical mass sprctrometry", *Nature Nanotechnology* 4, 445-450 (2009).

Rugar, D. et al., "Single spin detection by magnetic resonance force microscopy", *Nature* 430, 329-332 (2004).

Sampathkumar, A. et al. "Multiplexed Optical Operation of Distributed Nanoelectromechanical Systems Arrays", *Nano Lett.* 11, 1014-1019 (2011).

Zhang Z. et al.. "Rapid and label-free nanomechanical detection of biomarker transcripts in human RNA", *Nat. Nanotechnol.* 1, 214-220 (2006).

International search report and written opinion received in connection with related international application No. PCT/US2011/023283, dated Nov. 12, 2013.

* cited by examiner

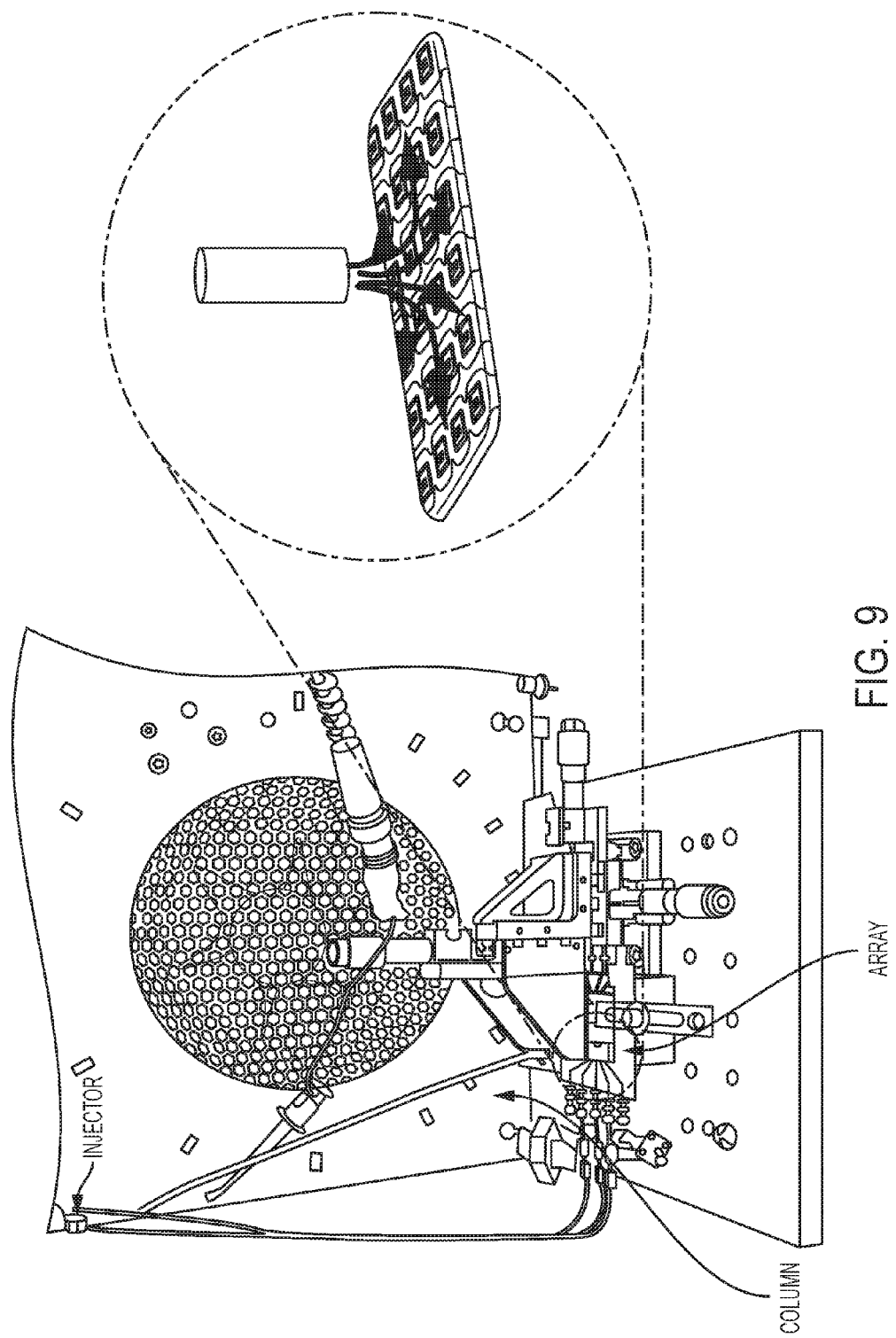

PIEZORESISTIVE NEMS ARRAY NETWORK

CROSS-REFERENCE TO RELATED APPLICATION

This application claims benefit of priority to U.S. Provisional Application No. 61/748,340 filed on Jan. 2, 2013, which is herein incorporated by reference in its entirety.

STATEMENT, FEDERALLY SPONSORED RESEARCH OR DEVELOPMENT

The U.S. Government has rights in this invention pursuant to grant number NBCH1050001 from DARPA/MTO-MGA.

BACKGROUND OF THE INVENTION

In the last several years, individual nanoelectromechanical resonators have been used to establish record sensitivities in force (Rugar, et al. *Nature* 2004, 430, 329-332), position (LaHaye et al., *Science* 2004, 304, 74-77), mass (Naik, et al., *Nat. Nanotechnol.* 2009, 4, 445-450; Jensen, et al., *Nat. Nanotechnol.* 2008, 9, 533-537), and gas concentration (Li et al., *Nat. Nanotechnol.* 2007, 2, 114-120). The miniscule size of nanoelectromechanical system (NEMS) or micoelectromechanical system (MEMS) sensors gives them unprecedented sensitivity to external perturbations, but this often comes at a cost. For example, both the power these devices can use and the magnitude of signal they can produce decrease at smaller sizes. Moreover for gas sensors, the interaction cross-section with particular analytes in a gas or liquid environment can rapidly decrease as the active mechanical element becomes smaller, whether due to increased analyte diffusion time, interaction with non-active sensor regions, or noisy, stochastic absorption/desorption of trace analyte levels (Arlett et al., *Nat. Nanotechnol.* 2007, 6, 203-15). In this limit of "needle in a haystack" detection, individual NEMS may have difficulty capturing even a single molecule of the analyte. Such challenges can make it difficult to exploit the full potential of individual NEMS sensors in the next generation of real-world microanalytical tools.

It is therefore desirable to scale up the interaction cross-section of NEMS sensors while still maintaining, or even enhancing, their extraordinary sensitivities and useful attributes. One approach to this task is simply to combine individual devices into arrays. For chemical sensors, different devices within the array can serve as detectors of different chemical compounds. Such arrays have previously been fabricated from microscale cantilever resonators (Zhang et al, *Nat. Nanotechnol.* 2006, 1, 214-220), microscale membrane resonators (Lee et al, *Proc. IEEE Sensors Conf* 2010, 2122-2126), nanoscale cantilevers (Li et al., *Nano Lett.* 2010, 10 3899-3903), nanoscale doubly clamped beam resonators (Sampathkumar et al., *Nano Lett.* 2011, 11 1014-1019), and nanowire resonators (Li et al., *Nat. Nanotechnol.* 2008, 3, 88-92).

Alternatively, one can use the collective response of multiple elements of the array to enhance the signal-to-noise ratio or other properties. For example, by engineering the mechanical coupling between individual resonators, one can produce a collective mode of oscillation that inherits the positive characteristics of individual resonators, such as high frequency and quality factor, but is able to handle more power (Li et al., Disk-array design for suppression of unwanted modes in micromechanical composite-array filters, *Tech. Digest, 19th IEEE Int. Conf on MicroElectroMechanical Systems (MEMS'06)*, Istanbul, Turkey, Jan. 22-26, 2006). Such collective modes can then be further optimized to produce the desired overall response, for example, that of a bandpass filter (Li et al, An MSI micromechanical differential disk-array filter, *Digest of Tech. Papers, 14th Int. Conf on Solid-State Sensors & Actuators (Transducers'07)*, Lyon, France, Jun. 11-14, 2007).

Despite these advances, presently available sensors are in many if not all cases still lacking in one or more factors such as, for example, ease of use, power handling, sensitivity and robustness.

SUMMARY OF THE INVENTION

Embodiments described herein include, among other embodiments, devices and methods of making and methods of using devices.

For example, one embodiment relates to a sensor for detecting an analyte. In one embodiment, the sensor comprises at least one array, with the array comprising a plurality of resonators. In one embodiment, the resonators are arranged in a plurality of rows and a plurality of columns. In one embodiment, the resonators in an array are about the same size and are adapted to independently vibrate at about the same resonance frequency and about the same phase. In one embodiment, the resonators in the array are electrically coupled in a series-parallel configuration. In one embodiment, at least one row of resonators is connected in parallel and at least one column of resonators is connected in series. In one embodiment, all resonators in a row are connected in parallel and all resonators in a column are connected in series.

In one embodiment, the resonators are adapted to interact with an analyte. In yet another embodiment, the analyte can be detected even if it is present at a parts per billion concentration.

One embodiment, in addition, relates to a method for using an article, comprising exciting resonators into vibration at a resonance frequency and detecting the vibration. In one embodiment, the vibration is detected before, during and/or after exposure to an analyte.

In one embodiment, the method is performed with an article wherein the resonators are a part an array, and wherein the resonators are electrically coupled using a combined series-parallel configuration, wherein at least one array is electrically connected to an actuator and a signal detector, wherein the resonators of the array are adapted to vibrate at the same frequency and the same phase, and wherein at least one resonator is functionalized for detection of at least one analyte.

In one embodiment, an article comprises: at least one array comprising a plurality of resonators. The resonators are arranged in a plurality of rows and a plurality of columns, and the resonators are adapted to vibrate at about the same resonance frequency and about the same phase.

In one aspect of the article, the resonators are cantilevers. In one aspect of the article, the resonators are nanoresonators. In another aspect of the article, the resonators comprise piezoresistors.

In one aspect of the article, the array comprises at least 1,000 resonators. In another aspect of the article, the array comprises at least 25,000 resonators. In another aspect of the article, the array comprises at least 100,000 resonators.

In one aspect of the article, the resonators in the array are substantially identical.

In one aspect of the article, the resonators are about 1.6 micrometers to about 5 micrometers long, and are about 800 nanometers to about 1.2 micrometers wide.

In one aspect of the article, the resonators are adapted to vibrate independently.

In one aspect of the article, the resonators are electrically coupled using a combined series-parallel configuration.

In one aspect of the article, the resonators are electrically coupled using a combined series-parallel configuration. At least one row of resonators is connected in parallel, and at least one column of resonators is connected in series.

In one aspect of the article, the resonators are electrically coupled using a combined series-parallel configuration, and all resonators of a row are connected in parallel and all resonators of a column are connected in series.

In one aspect, the article further comprises an actuator and a signal detector electrically connected to the array.

In one aspect of the article, the resonators are adapted to vibrate independently, and the resonators are adapted so that signals based on the resonator vibration are electrically coupled.

In one aspect of the article, the actuator is adapted to excite the resonators into vibration at a resonance frequency by electric actuation. In one aspect of the article, the actuator is adapted to excite the resonators into vibration at a resonance frequency by thermoelastic actuation.

In one aspect of the article, the signal detector is a piezoresistive signal detector.

In one aspect of the article, at least one metal loop is used for both actuation and signal detection.

In one aspect of the article, the metal loop comprises NICHROME metal, CONSTANTAN metal or MANGANINE metal.

In one aspect of the article, the article comprises multiple arrays that can be measured at the same time.

In one aspect of the article, the resonators of each array are adapted to resonate at a center frequency, and the resonators of each array are adapted to vibrate at a different center frequency than the resonators of other arrays.

In one aspect of the article, each resonator has a resistance of about 1Ω to about 20Ω. In one aspect of the article, each resonator has a resistance of about 7Ω.

In one aspect of the article, the plurality of rows and columns is arranged so that the total resistance of the array is about 1Ω to about 100Ω. In one aspect of the article, the plurality of rows and columns is arranged so that the total resistance of the array is about 50Ω.

In one aspect of the article, the array is able to handle power input of at least 900 mW per array.

In one aspect of the article, the article further comprises an analyte delivery system.

In one aspect of the article, the analyte delivery system comprises a chamber with a valve, and the array is exposed to an analyte by opening the valve.

In one aspect of the article, the analyte delivery system is a gas chromatography column that is connected to the array.

In one aspect of the article, the article is functionalized for detection of at least one analyte.

In one aspect of the article, the resonators are coated with a coating material capable of interacting with at least one analyte.

In one aspect of the article, the article comprises multiple arrays, the resonators are coated with a polymer capable of interacting with at least one analyte, and each array is configured to detect a single analyte.

In one aspect of the article, the article comprises multiple arrays, the resonators are coated with a polymer capable of interacting with at least one analyte. Each array is configured to interact with at least one analyte, and the article is configured to interact with at least two analytes.

In one aspect of the article, the article further comprises an actuator and a signal detector electrically connected to the array, and an analyte delivery system connected to the array. The resonators are functionalized for detection of at least one analyte, and the article is capable of detecting an analyte present at a parts per billion concentration.

In one aspect of the article, the resonators are distributed over at least a 100 $nm^2$ area.

In one aspect of the article, the array has a maximum resonator density of between 4 and 6 million resonators per square centimeter.

In one aspect of the article, the sensor is adapted for a single measurement circuit.

In one aspect of the article, the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

In one aspect of the article, the resonators are coated with a coating material capable of interacting with at least one analyte. The analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

In one embodiment, an article comprises: at least one array comprising a plurality of resonators, and the resonators are arranged in a plurality of rows and a plurality of columns. The resonators are electrically coupled using a combined series-parallel configuration, and all resonators of a row are connected in parallel and all resonators of a column are connected in series.

In one aspect of the article, the resonators are about the same size and the resonators are adapted to independently vibrate at about the same resonance frequency and about the same phase.

In one embodiment, an article comprises: at least one array comprising a plurality of resonators. The resonators are adapted to sense an analyte present at a part per billion concentration or less.

In one aspect of the article, the resonators are arrayed in columns and rows.

In one aspect of the article, the article is adapted for improved signal-to-noise ratios.

In one aspect of the article, the article is adapted for improved power matching.

In one aspect of the article, the article is adapted for improved power handling.

In one aspect of the article, the article is adapted for improved robustness.

In one aspect of the article, the resonators are arranged in columns and rows and are electrically coupled in a combined series-parallel configuration.

In one aspect of the article, the resonators are about the same size, and the resonators are adapted to independently vibrate at about the same resonance frequency and about the same phase.

In one aspect of the article, the resonators are functionalized for detection of at least one analyte.

In one aspect of the article, the resonators are adapted for measurement by a single circuit.

In one embodiment, a method comprises: exciting resonators into vibration at a resonance frequency; and detecting the vibration. The resonators are a part an array, and the resonators are arranged in a plurality of rows and a plurality of columns. The resonators in an array are adapted to vibrate at about the same resonance frequency and about the same phase, and at least one array is electrically connected to an actuator and a signal detector. At least one resonator is functionalized for detection of at least one analyte.

In one aspect of the method, the vibration is detected via a piezoresistor disposed on the resonators.

In one aspect of the method, the method further comprises exposing the article to an analyte.

In one aspect of the method, the method further comprises exposing the article to an analyte and detecting a shift in the resonance frequency of the array resulting from exposure to the analyte.

In one aspect of the method, the shift in the resonance frequency is due to an interaction between the functionalized resonator and the analyte.

In one aspect of the method, the article is exposed to the analyte for a period of two seconds or less.

In one aspect of the method, the analyte is present at a part per billion concentration or less.

In one aspect of the method, the resonators are cantilevers. In one aspect of the method, the resonators are nanoresonators. In one aspect of the method, the resonators are piezoresistors.

In one aspect of the method, the array comprises at least 1,000 resonators. In one aspect of the method, the array comprises at least 25,000 resonators. In one aspect of the method, the array comprises at least 100,000 resonators.

In one aspect of the method, the resonators are substantially identical.

In one aspect of the method, the resonators are about 1.6 micrometers to about 5 micrometers long. In one aspect of the method, the resonators are about 800 nanometers to about 1.2 micrometers wide.

In one aspect of the method, the resonators are electrically coupled using a combined series-parallel configuration.

In one aspect of the method, the resonators are electrically coupled using a combined series-parallel configuration, and all resonators of a row are connected in parallel and all resonators of a column are connected in series.

In one aspect of the method, the resonators are adapted to vibrate at about 15 MHz to about 30 MHz.

In one aspect of the method, the resonators are adapted to vibrate independently.

In one aspect of the method, the resonators are adapted to vibrate independently and signals based on the resonator vibration are electrically coupled.

In one aspect of the method, the resonators are excited into vibration by electric actuation.

In one aspect of the method, the resonators are excited into vibration by thermoelastic actuation.

In one aspect of the method, the signal is detected by a two-port downmixing measurement scheme.

In one aspect of the method, at least one metal loop is used for actuation and signal detection.

In one aspect of the method, at least one metal loop is used for actuation and signal detection, and the metal loop is made of NICHROME metal, CONSTANTAN metal or MANGANINE metal.

In one aspect of the method, the article comprises multiple arrays that can be measured at the same time.

In one aspect of the method, the article comprises multiple arrays that can be detected at the same time, and each array resonates at a center frequency. The article resonates at at least two center frequencies.

In one aspect of the method, each resonator has a resistance of about 1Ω to about 20Ω. In one aspect of the method, the plurality of rows and columns is arranged so that the total resistance of the array is about 1Ω to about 100Ω.

In one aspect of the method, the array is able to handle power input of at least 2 watts per array.

In one aspect of the method, the array is able to handle power input of at least 900 mW per array.

In one aspect of the method, the resonators are coated with a polymer capable of interacting with at least one analyte. In one aspect of the method, the article comprises multiple arrays, and the resonators are coated with a polymer capable of interacting with at least one analyte. Each array is configured to detect a single analyte.

In one aspect of the method, the article comprises multiple arrays, and the resonators are coated with a polymer capable of interacting with an analyte. The article is configured to detect a single analyte.

In one aspect of the method, the article comprises multiple arrays, and the resonators are coated with a polymer capable of interacting with at least one analyte. Each array is designed to interact with at least one analyte, and the article is configured to interact with at least two analytes.

In one aspect of the method, the resonators are distributed over an at least 100 nm$^2$ area. In one aspect of the method, the array has a maximum resonator density of between 4 to 6 million resonators per square centimeter.

In one aspect of the method, the at least one array is connected in a single circuit.

In one aspect of the method, the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

In one embodiment, an article comprises: at least one array comprising a plurality of resonators, and the resonators are arranged in a plurality of rows and a plurality of columns. The resonators are electrically coupled using a combined series-parallel configuration, and all resonators of a row are connected in parallel and all resonators of a column are connected in series. The resonators are adapted to vibrate independently at about the same resonance frequency and about the same phase. An actuator and a signal detector are also electrically connected to the array, and the actuator is configured to excite the resonators by electric actuation. The detector is a piezoresistive detector. An analyte delivery system is also connected to the article, and the article is functionalized for detection of at least one analyte.

In one aspect of the article, the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

BRIEF DESCRIPTION OF THE DRAWINGS

FIG. 9 shows integration of an array sensor into a commercial Hewlett-Packard 5890 gas chromatography system, and the inset is a schematic showing a gas delivery system positioned above an array and illustrating how effluent flows to the array.

DETAILED DESCRIPTION

All references cited in this application are incorporated herein by reference in their entireties. In particular, the article, Bargatin et al., *Nano Lett.*, 2012, 12, 1269-1274 provides additional guidance and is incorporated by reference in its entirety.

Resonator Array

Some embodiments described herein relate to a microelectromechanical system (MEMS) or nanoelectromechanical system (NEMS) sensor comprising at least one array of resonators. MEMS and NEMS include devices with features having a size of 1 micron to 100 microns and 1 nanometer to less than 1 micron, respectively, in at least one dimension, and preferably in two or three dimensions (FIG. 3A-G). Embodiments of the present invention are believed to represent the first application of large-scale-integrated (LSI) fabrication techniques to NEMS or MEMS array fabrication, which utilizes the collective response of a plurality of electrically connected resonators to enable new paradigms in NEMS-based and MEMS-based sensing. Some embodiments of the present invention can utilize the essentially coherent response of a plurality of independent resonators, connected electrically in a manner that provides natural noise averaging, increased collective power handling capability, and fault-tolerant robustness. LSI-NEMS and MEMS arrays, while dramatically increasing the interaction cross-section of individual resonators, provides a potential route to orders-of-magnitude sensitivity improvements over individual resonator elements.

Any resonator or device suitable to provide a mechanical response may be utilized in the present invention, such as, for example, vibrational resonators, counter rotating and rotating resonators, torsional resonators, or compound resonators. For simplicity, all such potential devices will be hereafter referred to as "resonators".

The resonator can have physical properties suitable for detection of an analyte. For example, the resonators may be made of any suitable material, such as inorganic materials, including semiconductor materials, such as Si, SiC, III-V and II-VI materials, insulating materials, such as metal or semiconductor oxides, nitrides or carbides, including SiN and $SiO_2$, glass and even organic materials, such as polymeric/plastic materials. Resonators can be made of pure metals or metal alloys. For example, the resonators may be made of pure metals that include, but are not limited to, copper, nickel, platinum, aluminum, chromium, tungsten, palladium, silver and gold. Resonators can also be made of metal alloys. Examples of such alloys include, but are not limited to, CONSTANTAN metal, Karma, gold/palladium, and alloys based on the pure metals listed above. Examples of suitable metals and alloys are listed in Andreucci et al. (WO 2011/006885).

Figure 2A:
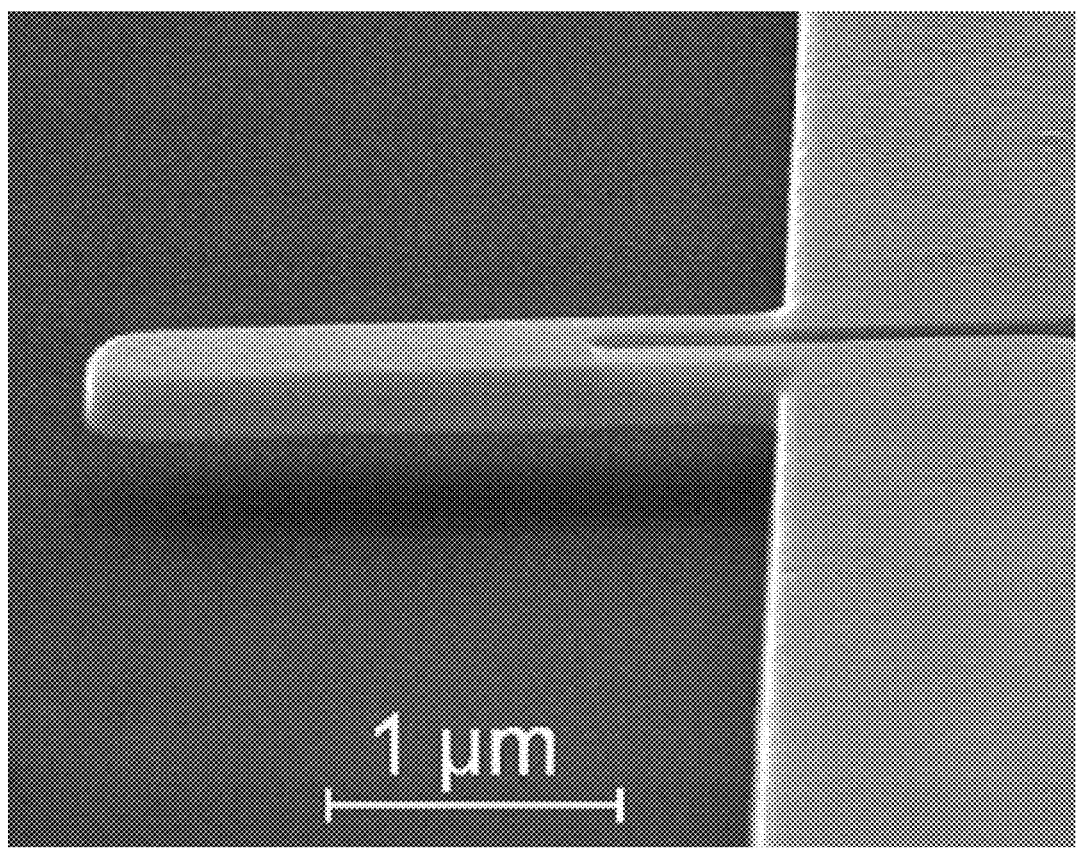
FIG. 2A is a scanning electron micrograph of an individual array component.
Figure 2B:
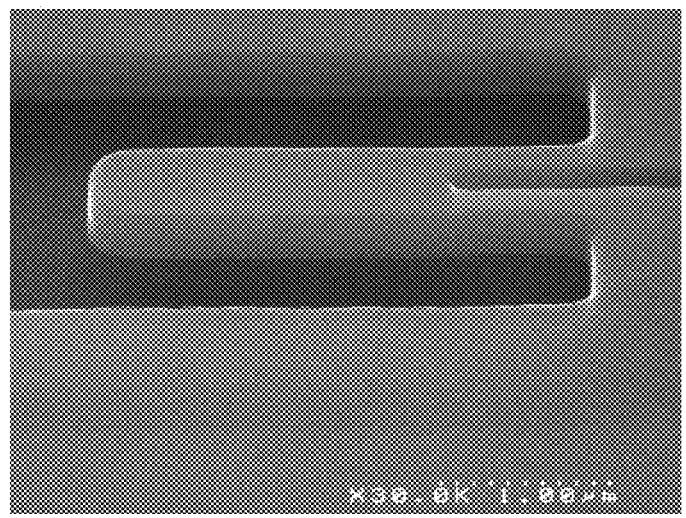
FIG. 2B is a scanning electron micrograph of a resonator with one metal loop.
Figure 2C:
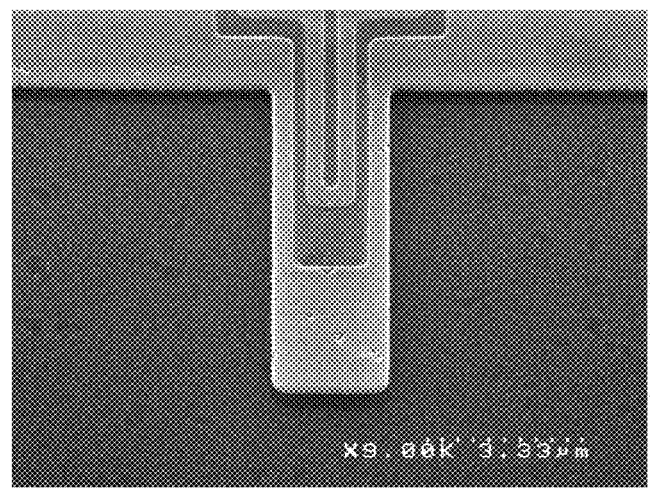
FIG. 2C is a scanning electron micrograph of a resonator with two metal loops.

In one embodiment, the resonator is a vibrating cantilever of simple or complex geometry. The resonator preferably comprises a micron or nanometer sized cantilever (FIGS. 2A-C). For example, the resonators can have a length of about 1.6 to about 5 micrometers. In one embodiment, the resonators can have a length of about 2 micrometers. In one embodiment, all resonators in the array are about the same length. For example, the lengths of all the resonators in the array may be within about 10% of one another, within about 5% of one another, or preferably within about 1% or 2% of one another.

In one embodiment, the resonators have a width of about 800 nanometers to about 1.2 micrometers. In one embodiment, the resonators are about 800 nanometers wide. In one embodiment, all resonators in the array are about the same width. For example, the widths of all the resonators in the array may be within about 10% of one another, within about 5% of one another, or preferably within about 1% or 2% of one another.

In one embodiment, all resonators in the array are substantially the same length and substantially the same width. For example, the lengths and widths of all the resonators in the array can be within about 10% of one another, within about 5% of one another, or preferably within about 1% or 2% of one another.

In one embodiment, the resonators have a thickness of about 10 nanometers to about 1 micrometer. The resonators can have a thickness of, for example, about 10 nm to about 500 nm, about 50 nm to about 250 nm, about 75 nm to about 150 nm, or about 100 nm. In one embodiment, all resonators in an array are about the same thickness. For example, the thicknesses of all the resonators in the array may be within about 10% of one another, within about 5% of one another, or preferably within about 1% or 2% of one another.

In one embodiment, the array comprises more than 1,000 resonators. In one embodiment, the array comprises more than 25,000 resonators. In one embodiment, the array comprises more than 100,000 resonators.

The array can be any size suitable for detection of analytes. For example, the array can cover a nanometer square area, a micrometer square area, a millimeter square area, or a centimeter square area. In one embodiment, the array can be at least about 100 nm$^2$, at least about 1 µm$^2$, at least about 20 µm$^2$, at least about 100 µm$^2$, at least about 200 µm$^2$, at least about 500 µm$^2$, or at least about 10 mm$^2$.

The minimum and maximum density of resonators on the array is not particularly limited. The maximum density of resonators in the array is based on the fabrication tolerance of the array. In one embodiment, the maximum resonator density is at least 1 million resonators per square centimeter, or at least 2 million resonators per square centimeter, or at least 4 million resonators per square centimeter, and preferably between 4 and 6 million resonators per square centimeter.

In a preferred embodiment, the resonators are piezoresistors. Resonators can have any resistance. In one embodiment, resonators have a resistance of about 1Ω to about 20Ω. In one embodiment, resonators have a resistance of about 5Ω to about 10Ω. In one embodiment, resonators have a resistance of about 7Ω.

Resonators can be adapted to vibrate at a resonance frequency. Resonance is the tendency of a system to oscillate with greater amplitude at some frequencies than at others. Frequencies at which the response amplitude is at a relative maximum are known as the system's resonance frequencies. At these frequencies, even small periodic driving forces can produce large amplitude oscillations. Resonators can be adapted to vibrate at a specific resonance frequency based on the length, width, thickness or material of the resonator.

In one embodiment of the present invention, all resonators in the array are adapted to vibrate with the same resonance frequency when excited by an actuator. In one embodiment, the resonators are adapted to vibrate at about 1 MHz to about 100 MHz when excited by an actuator. In one embodiment, the resonators are adapted vibrate at about 5 MHz to about 50 MHz when excited by an actuator. In one embodiment, the resonators are adapted vibrate at about 15 MHz to about 30 MHz when excited by an actuator. In one embodiment, resonators are adapted vibrate at about 24 MHz when excited by an actuator. In one embodiment, each resonator is adapted to vibrate independently from, but with about the same resonance frequency as, the other resonators in the array.

When a resonator vibrates, it vibrates at both a frequency and a phase. In one embodiment, resonators are adapted to vibrate independently from other resonators in the array and all resonators in the array are adapted vibrate at about the same frequency and about the same phase. In one embodiment, at least 70% of the resonators in the array are adapted to vibrate at about the same frequency and about the same phase. In one embodiment, at least 80% of the resonators in the array are adapted to vibrate at about the same frequency and about the same phase. In one embodiment, at least 90% of the resonators in the array are adapted to vibrate at about the same frequency and about the same phase. In one embodiment, at least 98% of the resonators in the array are adapted to vibrate at about the same frequency and about the same phase.

In one embodiment of the present invention, resonators are adapted to have an improved signal-to-noise ratio (SNR) when actuated to vibrate with coherent frequencies and phases.

Figure 1A:
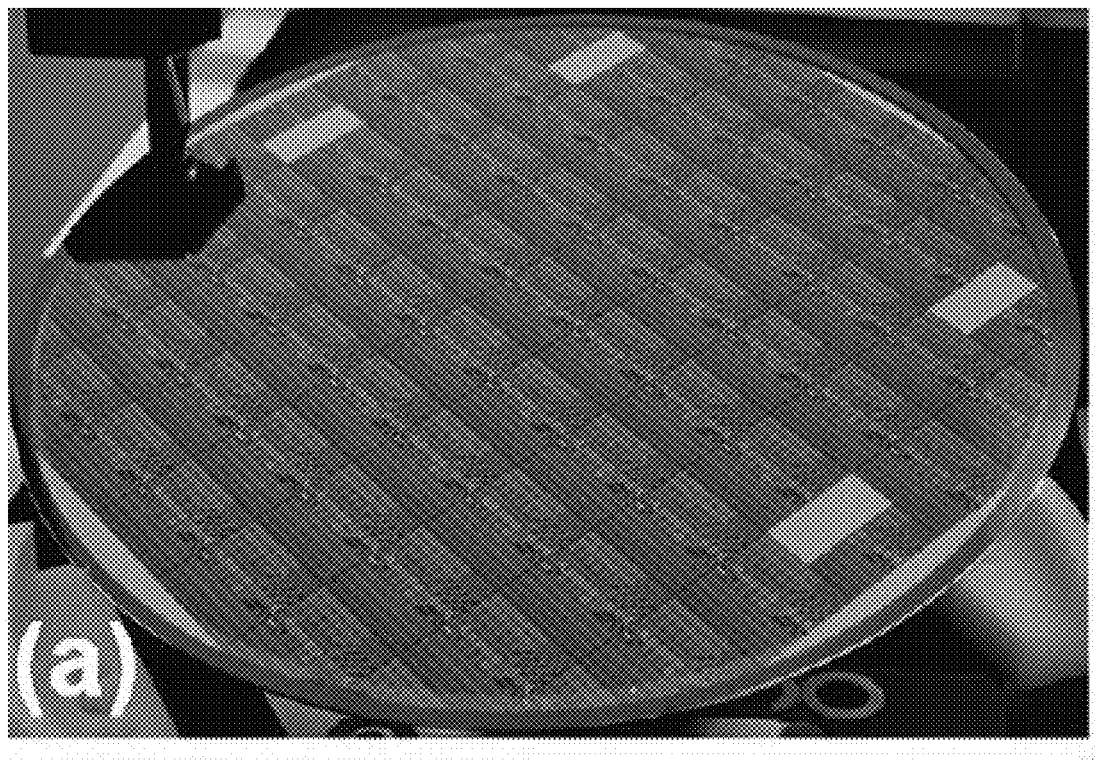
FIG. 1A is a photograph of a 200 mm wafer with patterned NEMS arrays.
Figure 1B:
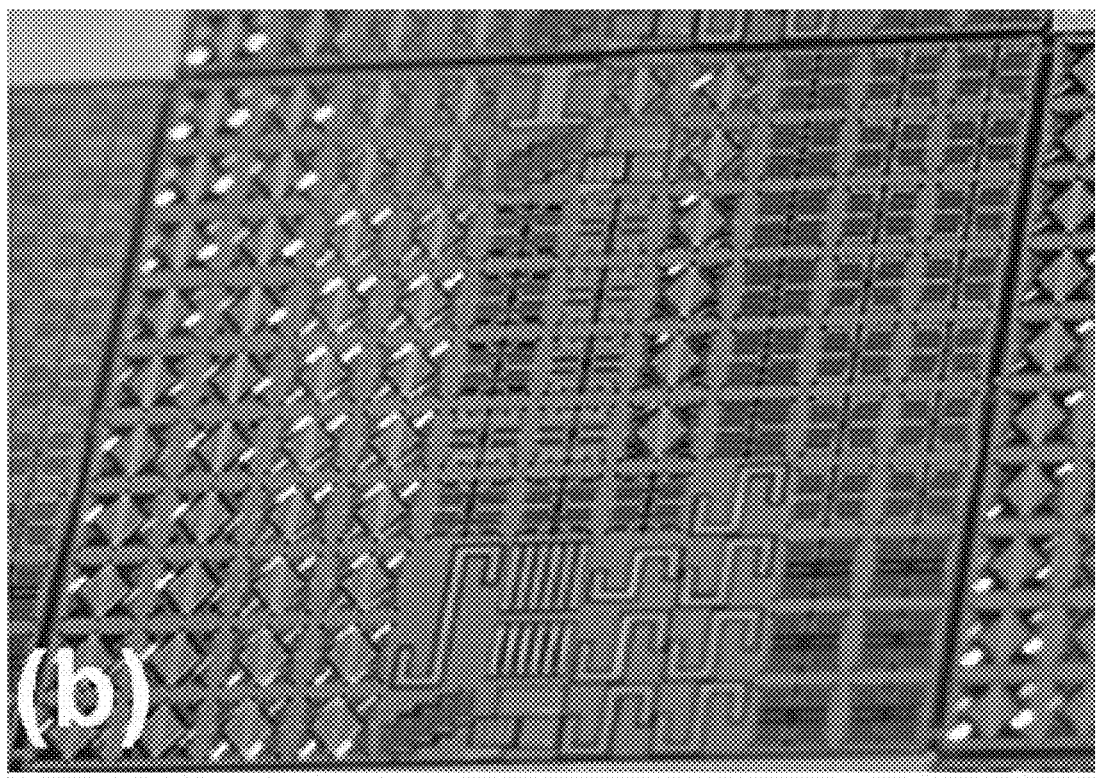
FIG. 1B is a zoomed-in photograph of a 20 mm wafer die containing a variety of nanofabricated resonator array structures.

In one embodiment, the sensor comprises multiple arrays (FIG. 1A-B). In one embodiment, the resonators in the multiple arrays are all adapted to vibrate at about the same resonance frequency and about the same phase. For example, the resonance frequency of the resonators may be within 10% of one another, preferably within 5% of one another, or more preferably within 1% of one another. In one embodiment, the sensor is comprised of multiple arrays, wherein each array is adapted to have different center frequencies from the other arrays but similar overall resistances. In one embodiment, multiple arrays are adapted so that the resonance frequency from each array can be detected at the same time. In one embodiment, multiple arrays are configured to allow for balanced detection of the arrays.

Resonator Configuration

The resonators in the array can be connected electrically. Resonators can be electrically connected in series, in parallel or in a combined series-parallel configuration. In one embodiment, the array comprises rows and columns of resonators that are electrically connected. In one embodiment, at least one row of resonators in an array is connected in parallel. In one embodiment, at least two rows of resonators in an array are connected in parallel. In one embodiment, at least 25%, at least 50% or at least 75% of rows are connected in parallel. In one embodiment, all rows of resonators are connected in a parallel configuration.

In one embodiment, at least one column of resonators is connected in series. In one embodiment, each column of resonators is connected in a series configuration.

In one embodiment, rows are connected in a parallel configuration and columns are connected in a series configuration. In one embodiment, shown, for example, in FIG. 3G, all rows are connected in a parallel configuration and all columns are connected in a series configuration. In one embodiment, all columns are connected in series configurations and at least one row is connected in a parallel configuration.

In one embodiment, the resonators in an array are connected so that the array functions as a single resonator. In one embodiment, multiple arrays are connected so that the multiple arrays function as a single resonator. In one embodiment, each array comprises a single circuit. In one embodiment, multiple arrays comprise a single circuit. In one embodiment, each column comprises a single circuit, and signals from each circuit are combined using data processing steps.

In one embodiment, an advantage of combining columns and rows in a series-parallel configuration array is that the array can be used as a sensor even if most individual resonators prove defective, as long as there remains a conductive pathway through the array.

In one embodiment, an advantage of embodiments of the present invention is improved power matching. For example, total resistance of an array consisting of l rows and m columns can be given by (mr)/l. It is therefore possible to produce impedance-matched arrays from a wide range of individual resonators by changing the row and column count. In one embodiment, the number of rows and columns is adapted so that the total resistance of the array is about 1Ω to about 100Ω. In one embodiment, the number of rows and columns is adapted so that the total resistance of the array is about 25Ω to about 75Ω. In one embodiment, the number of rows and columns is adapted so that the total resistance of the array is about 45Ω to about 60Ω. In one embodiment, the number of rows and columns is adapted so that the total resistance of the array is about 50Ω.

The array can have, for example, from about 2 to about 100 rows, from about 20 to about 80 rows, from about 30 to about 50 rows, or about 40 rows. The array can have, for example, from about 2 to about 300 columns, from about 50 to about 250 columns, from about 100 to about 200 columns, from about 120 to about 180 columns, from about 130 to about 150 columns, or about 140 columns.

In one embodiment, an advantage is increased collective power handling capabilities. In general, arrays can handle powers that are larger by a factor of N, wherein N is the total number of array elements. In one embodiment, the array is adapted to handle maximum powers of more than about 900 mW. In one embodiment, the array is adapted to handle maximum powers of more than about two watts. In one embodiment, the array is adapted to handle maximum powers of more than about five watts. In one embodiment, the array is configured to handle maximum powers of more than about ten watts.

In one embodiment, an advantage is an increase in the SNR of the measured response. More specifically, one benefit of the present invention relates to how the measured response of the entire array relates to the measured response of the individual resonators. The relative change in the resistance of the array is the average of the relative change in the resistance of individual array elements:

$$\frac{\Delta R_{arr}}{R_{arr}} \approx \frac{1}{N}\sum_{i=1}^{l}\sum_{j=1}^{m}\frac{\Delta r_{ij}}{r} \qquad \text{(Equation 1)}$$

where $r$ is the at-rest resistance, $\Delta r_{ij}$ is the change of the resistance of the resonator situated in the ith row and jth column of the array and $N=lm$ is total number of array elements. The resistance contribution from each resonator $\Delta r_{ij}$ is a combination of mechanical signal and aggregate noise (e.g., Johnson noise, phase noise, thermal fluctuation noise). However, if every element of the NEMS array is substantially identical, that is, if all element signals are at the same frequency and phase, then signal and noise do not add similarly in Equation (1). Rather, the mechanical signals will sum coherently, while many of the individual resonator noise contributions add together incoherently. In the ideal case of substantially identical resonators driven at the same frequency and phase, the signal-to-noise ratio scales as the square root of the number of array elements. For arrays comprised of thousands of elements, this can result in orders of magnitude improvement in SNR for resonator arrays vs. single resonators.

Figure 6A:
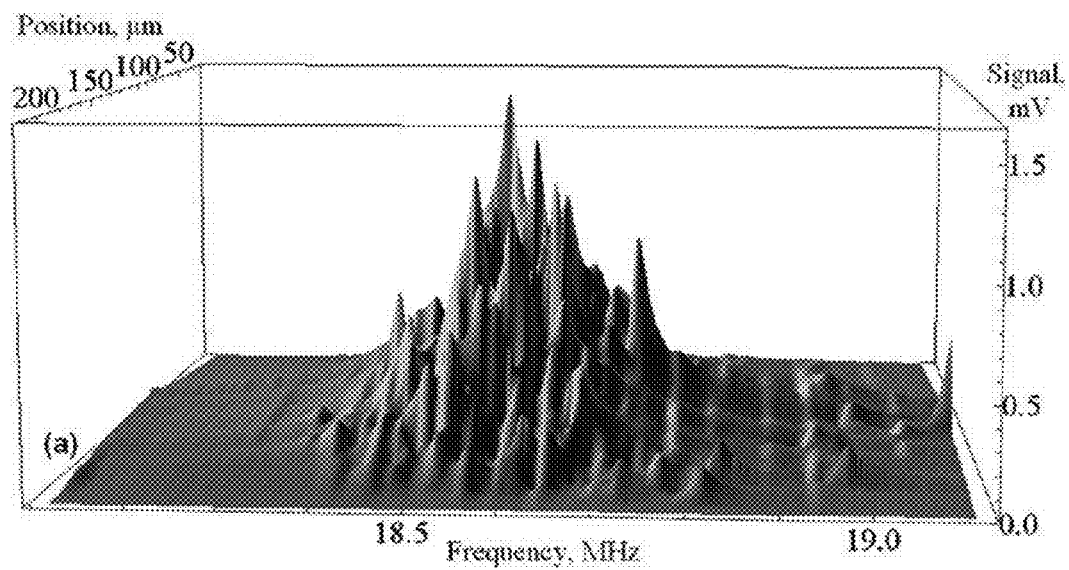
FIG. 6A is an optically detected spectrum of resonators in a representative array.

Imperfect frequency uniformity also yields enhanced SNR over that of single resonators. The frequency response of such an array is approximately described by a Lorentzian, just like in the case a single driven harmonic oscillator (FIG. 6A). However, an effective quality factor, $Q_{eff}$, of the array response is set by both the individual element quality factor, Q, and the width of the resonance frequency distribution, $\Delta f$, of the array. $Q_{eff} \approx 1/(Q^{-1}+Q_{distr}^{-1})$, where $Q_{distr} \approx f/\Delta f$ describes the relative magnitude of resonance frequency dispersion across the array.

In one embodiment, dispersion of the resonance frequency across the array, as measured using thermoelastic actuation and optical detection, is on the order of 10% or less. In yet another embodiment, dispersion of the resonance frequencies across the array is on the order of 5% or less. In one embodiment, dispersion of resonance frequencies across the array is on the order of 1% or less, corresponding to $Q_{distr} \approx 100$.

Actuation and Signal Detection

In one embodiment, an article can comprises an actuator. The actuator can excite the resonators into vibration. Preferably, the actuator is an integrated actuator. In one embodiment, the actuator can excite the resonators using electrothermally generated strain. The electrothermally generated strain can be induced by, for example, purely electric actuation. In one embodiment, actuation is by thermoelastic excitation.

In one embodiment, the actuator can be a capacitive actuator. In one embodiment, the actuator can be a piezoelectric actuator. In one embodiment, the actuator can be an optical actuator.

Preferably, each resonator can be actuated with essentially identical driving phases. Phase coherence provides power handling and signal-to-noise ratio benefits over traditional resonator arrays.

In one embodiment, the array further comprises a signal detector. Any detector suitable for detecting the resonance motion of the resonators may be used. For example, the detector may comprise a vibrational or strain sensitive device integrally connected to the resonator.

In one embodiment, the motion of the resonators is detected electrically. In one embodiment, the detector can be a capacitive detector. In one embodiment, the detector can be a piezoelectric detector. In one embodiment, the resonator vibration can be detected electrically through a metal surface layer's piezoresistive response. For example, the detector can be a piezoresistive strain transducer that converts the motion of the resonator into an electrical signal via the strain-induced change in resistance of a conducting path involving the resonator.

Signal detection can be performed by doing a frequency sweep to determine the signal detected at each frequency.

In one embodiment, a single-port connection to the array can be made through electrodes. In one embodiment, the electrodes are on opposite edges of the array. In one embodiment, actuation and detection can be done using a two-port connection. In one embodiment, actuation and detection can be done using a four-port connection.

In another embodiment, the detector may comprise an externally mounted device, such as an optical-laser, fluorescence based position sensor, or electromagnetic or magnetic sensor.

Measurement Scheme

Figure 4A:
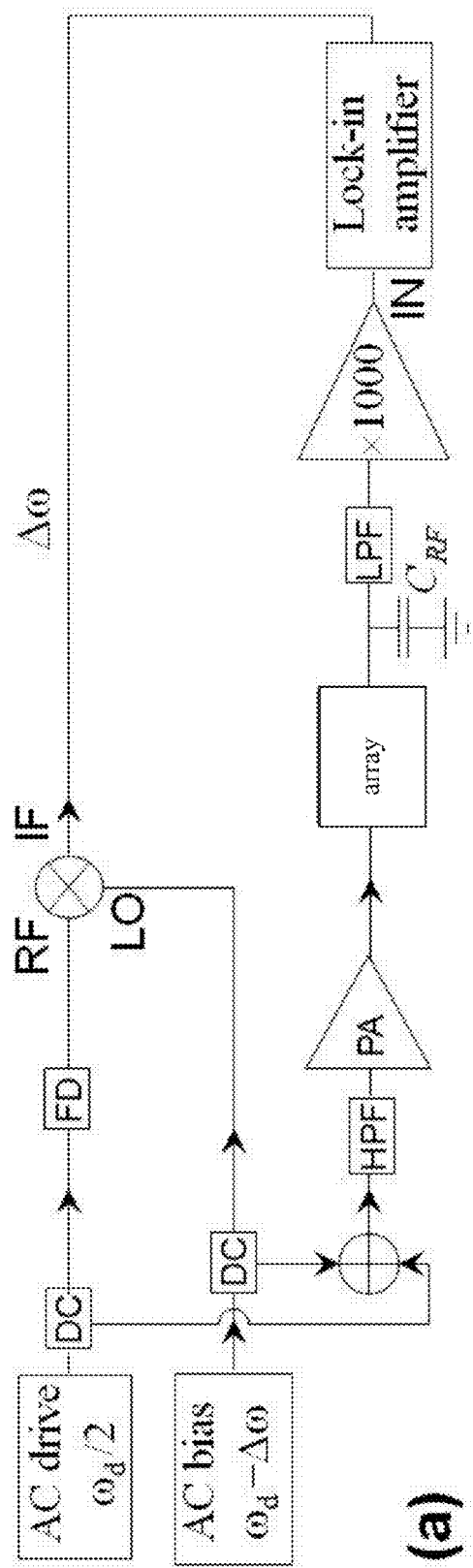
FIG. 4A is a schematic of a two-port measurement of an array using thermoelastic actuation and piezoresistive detection.
Figure 4B:
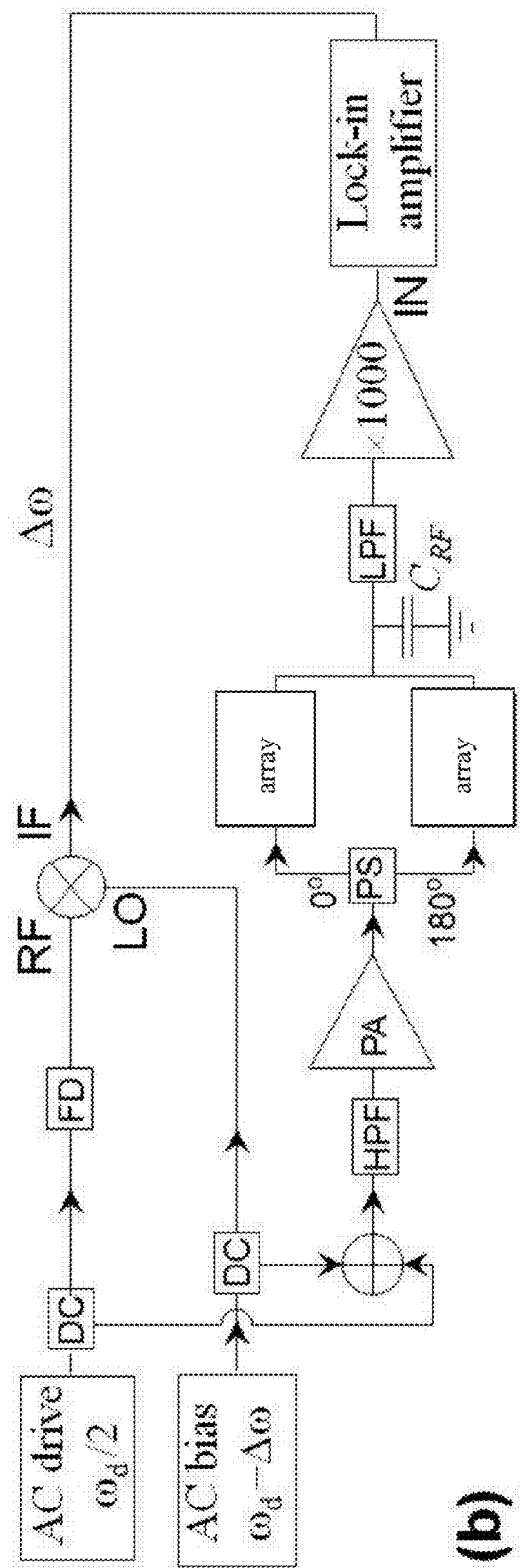
FIG. 4B is a schematic of a two-port measurement of multiple arrays using thermoelastic actuation and piezoresistive detection and with balanced detection of the arrays.

The measurement of the resonator motion can be via open loop measurement. In one embodiment, the measurement of the resonator motion can be via a closed loop measurement. The motion of the array resonators can be actuated and detected using a two-port downmixing measurement scheme (FIG. 4A-B) or a four-port downmixing measurement scheme. In a two-port scheme, a single metal loop is used. In a four-port scheme, two metal loops are used.

In one embodiment, resonator motion is induced with a drive voltage oscillating at frequency $\omega_d/2$, which creates temperature variations at frequency $\omega_d$. A bias voltage frequency $\omega_b$ can be offset from the drive frequency, $\omega_b=\omega_d-\Delta\omega$. In one embodiment, this offset is by less than 100 kHz. Both the drive and bias voltages can be combined using an RF power combiner and sent into the metal loop.

On the other side of the loop, an RF capacitor can be connected to the ground. In one embodiment, a relatively large RF capacitor is connected to ground and therefore creates a virtual ground at high frequencies. For example, if a 6 nF capacitor is connected to the ground, then $f >> (2\pi \times 50\Omega \times 6 \text{ nF})^{-1} \approx 500$ kHz. This ensures that both the drive and bias voltages primarily drop across the metal loop of the resonator rather than elsewhere in the circuit. In one embodiment, a low-pass filter can be used to ensure that only the downmixed signal, and not the RF drive and bias voltages, are transmitted into a low-noise amplifier.

In one embodiment, a high pass filter can be used to filter out coupling to low frequency signals before resonator motion is induced.

In one embodiment, the array further comprises a means of reducing background nmse. The source of this background noise is not limited, and can be for example strain and/or temperature. In one embodiment, background noise is reduced by fabricating the metal loop with alloys having temperature coefficients of resistance up to one order of magnitude smaller than that of pure metals. In another embodiment, the alloys have temperature coefficients up to two orders of magnitude, up to three orders of magnitude, or up to four orders of magnitude smaller than that of pure metals. In one embodiment, the temperature coefficient of the alloy is from about ±10-2 to about ±10-7 (units of fractional resistance change per ° C.). The metal loop can be made of any suitable alloy, for example NICHROME metal, CONSTANTAN metal or MANGANINE metal.

In one embodiment, two separate thermally isolated loops are used for actuation and detection (FIG. 2C).

A four port measurement scheme is described, for example, in I. Bargatin, I. Kozinsky, M. L. Roukes, *Efficient electrothermal actuation of multiple modes of high-frequency nanoelectromechanical resonators*, Appl. Phys. Lett. 90, 093116 (2007).

Figure 5:
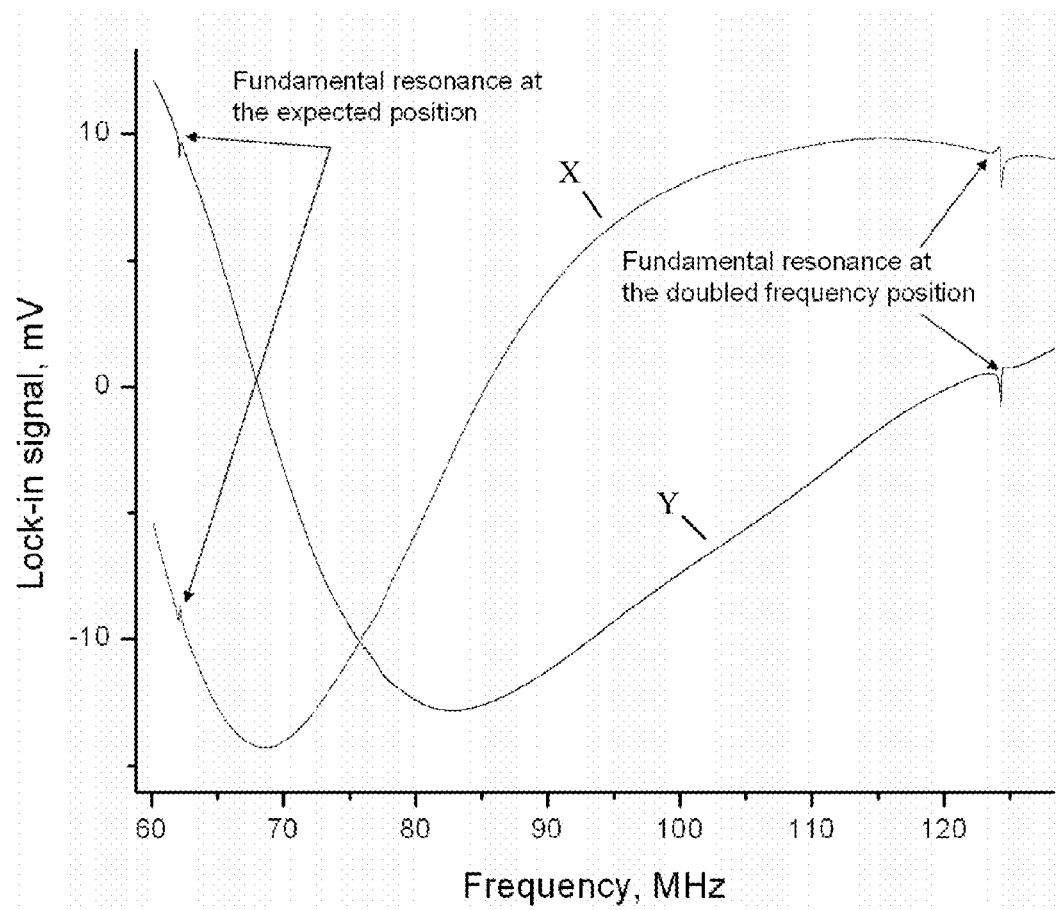
FIG. 5 shows a wide frequency sweep for a two-port measurement of a single resonator.

In a two-port measurement, two peaks are detected during detection (FIG. 5). The first peak appears at the expected position, where the voltages are applied at the frequencies $\omega_1=\omega_d/2=\omega_R/2$ and $\omega_2=\omega_b=\omega_R-\Delta\omega$, where $\omega_R$ is the resonance frequency. A second peak appears when one voltage is applied at the frequency $\omega_1=\omega_R+\Delta\omega$ and another at $\omega_2=2\omega_R+\Delta\omega$. When both of these voltages are applied to the same loop, they will mix and produce temperature variations at the difference frequency $\omega_2-\omega_1=\omega_R$, therefore driving the resonance. The resistance variations at frequency $\omega_R$ can then mix with the applied voltage at frequency $\omega_1=\omega_R+\Delta\omega$ to produce a signal at the expected downmixed frequency $\Delta\omega$. The net result is that another peak appears in the graph at roughly twice the frequency of the expected peak.

Surprisingly, the amplitude of the additional peak is often approximately twice the size of the expected peak. This can be explained by considering the algebraic relationships of the various voltage-mixing processes involved. If we apply a sum of two voltages oscillating at frequencies $\omega_1$ and $\omega_2$, the heating is proportional to the square of total voltage:

$$\Delta T = (V_1\cos\omega_1 t + V_2\cos\omega_2 t)^2 \quad \text{(Equation 2)}$$
$$= V_1^2\cos^2\omega_1 t + 2V_1 V_2\cos\omega_1 t\cos\omega_2 t + V_2^2\cos^2\omega_2 t$$
$$= \frac{1}{2}V_1^2\cos 2\omega_1 t + V_1 V_2\cos(\omega_1-\omega_2)t + \frac{1}{2}V_2^2\cos 2\omega_2 t + \ldots$$

Therefore, the temperature variations at frequency $\omega_2-\omega_1$ are twice as big as those at frequency $\omega_1$, and therefore drive the resonator motion with twice as much force. The additional mixing process that produces the downmixed signal at frequency $\Delta\omega$ does not change that conclusion: the amplitude of "double-frequency" peak is twice that of the "regular" peak.

In addition to the twofold difference in amplitude, the phase of the resonance response of the additional peak is flipped with respect to that of the expected peak for reasons similar to those described as in the preceding section. As a result, the regular peaks are fitted with positive quality factors, while additional "double-frequency" peaks are fitted with negative quality factors. This is helpful when analyzing data from wide measurement sweeps that contain peaks from multiple mechanical resonances: if the fitted quality factor Q is positive, then there is a mechanical resonance at the expected frequency $\omega_e=\omega_1=\omega_2+\Delta\omega$; however, if the fitted Q is negative, the real mechanical resonance happens at the frequency $\omega_e/2-\Delta\omega$. In sensing applications, it is often more convenient to work with this "double-frequency" resonance peak since its signal-to-noise ratio is usually twice the size for the same amount of heating.

Figure 7A:
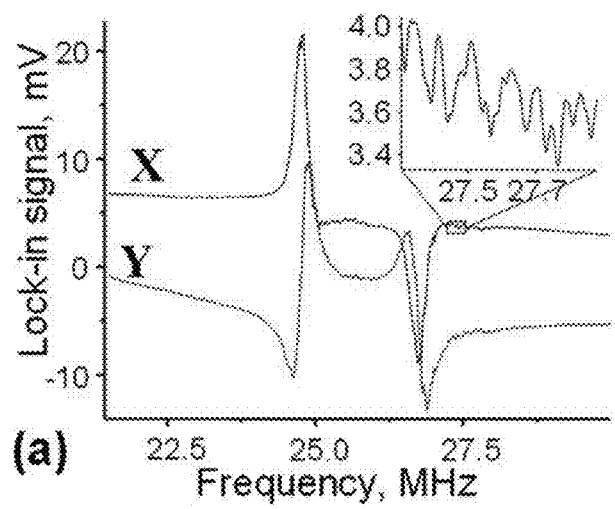
FIG. 7A is a resonant response of arrays in a vacuum.
Figure 7B:
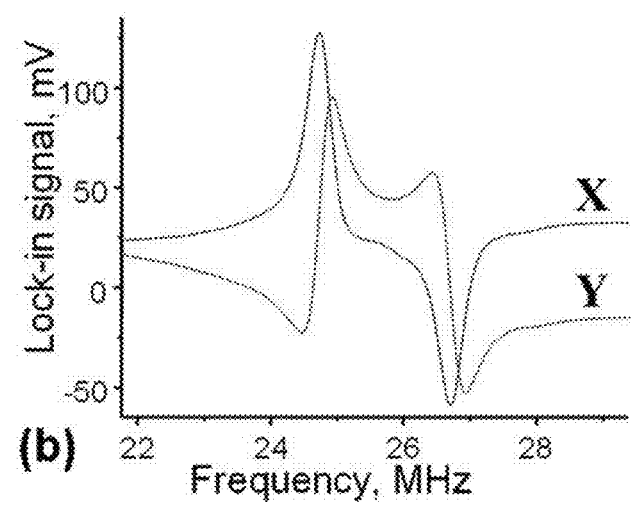
FIG. 7B is a resonant response of arrays in air.

In one embodiment, a balanced measurement scheme is used to measure signals from at least two arrays that have different center frequencies but similar overall resistances. In a balanced measurement scheme, coherent backgrounds generated in each array cancel each other out, but the resonance responses do not because the resonances occur at different frequencies for the two arrays. FIG. 7A-B show typical resonance responses measured in vacuum and air, respectively, using two arrays with resonators of nominal lengths of 2.0 μm and 2.1 μm. The graph features two resonance peaks, with the lower-frequency peak corresponding to the array with longer resonators and vice versa.

Piezoresistive Signal from Series-Parallel Arrays: Theoretical Framework

If it is assumed that, with no excitation, all piezoresistors have identical resistances $R_0$, the resistance of the entire array without excitation is given by $R_{arr}=R_0 \times m/l$, where m is the number of columns in the array, and l is the number of rows. If the resonators are excited into motion, the resistance of a piezoresistor in row i and column j will become $R_{ij}=R_0(1+\delta_{ij})$, where $\delta_{ij}$ is the relative change in its resistance due to the motion-related deformation. The resistance of the entire array in this case is given by $$R_{arr} = \sum_{j=1}^{m}\frac{1}{\sum_{i=1}^{l}R_0(1+\delta_{ij})^{-1}} \approx R_0\frac{m}{l}\left(1+\frac{1}{lm}\sum_{i=1}^{l}\sum_{j=1}^{m}\delta_{ij}\right) \quad \text{(Equation 3)}$$

where the Taylor expansion is justified because the relative changes in the resistance of piezoresistors are generally small, $\delta_{ij}\ll 1$. When using piezoresistive detection, the signal is proportional to the applied bias voltage $V_b$:

$$V_{arr} = \frac{1}{2}V_b\frac{\Delta R_{arr}}{R_{arr}} = \frac{V_b}{2lm}\sum_{i=1,j=1}^{l,m}\delta_{ij} \quad \text{(Equation 4)}$$

If all resonators respond in exactly identical ways, $\delta_{ij}=\delta_0$, the formula for the array signal reduces to that of an individual resonator:

$$V_{arr} = \frac{V_b}{2lm}\sum_{i=1,j=1}^{l,m}\delta_{ij} = \frac{1}{2}V_b\delta_0 \quad \text{(Equation 5)}$$

The maximum drive that can be applied to an individual piezoresistive resonator is limited either by the nonlinearity of mechanical response or the maximum tolerable level of heating. In our experiments, the maximum tolerable temperature increase due to heating is typically on the order of 100 K, corresponding to maximum dissipated power on the order of $P_{max}$~100 μW for an individual resonator. If this maximum power is applied to each resonator in the array, the total dissipated power will naturally scale as the number of array elements, N=lm. In contrast, the bias signal, $V_b$, and the maximum signal that can be obtained from the array, $V_{arr}$, will scale as the number of columns, m.

It would seem then that an array consisting of just one row would be the most economical way to leverage the signal of individual resonators. However, having an array of just one row would mean that the array resistance scales linearly with the number of array elements, $R_{arr}=R_0 \times N$, and may reach excessively large values for arrays of thousands of resonators. In experiments, it is often desirable to keep the resistance of the total array close to some fixed value, for example 50 Ohms for high-frequency applications. In addition, a single-row array is very vulnerable to electrical defects since the breaking of the conducting path in just one piezoresistor would render the entire array inoperable. As a result, it is preferable to scale the number of rows proportionally to the number of columns, so that the arrays remain robust with respect to defective individual resonators and have approximately constant resistance. In this case, the piezoresistive signal scales proportionally to m and therefore proportionally to the square root of the total number of array elements, $\sqrt{N}$. At the same time, Johnson noise and thermoelastic noise—the fundamental sources of noise in such measurement—do not depend on N at all. The signal-to-noise ratio then also scales as the square root of the number of elements, $\sqrt{N}$, and, of the total dissipated power, $\sqrt{N} P_{max}$. This situation, where the signal-to-noise ratio increases proportionally to the square root of the total dissipated power, is commonly encountered in electrical engineering.

Note, however, that the scaling of signal as $\sqrt{N}$ is the best-case scenario. In reality, different resonators will not respond to the drive in identical ways for a number of reasons. The first one to consider is that the phase and amplitude of the drive may not be the same for all resonators. For example, in the case of piezoshaker drive, the phases and amplitudes of the surface motion will vary due to the interference of ultrasound waves inside the bulk of the resonator chip. The length scale of such variations is on the order of the bulk acoustic wavelength corresponding to the resonator's frequency, ~350 μm for a 25 MHz resonator on silicon substrate.

If the drives for different resonators of the array have completely random phases $\phi_d$ but the same amplitude, then the array signal will take the form $$V_{arr} = \frac{1}{2} V_b \frac{\Delta R_{arr}}{R_{arr}} = \frac{V_b}{2lm} \sum_{i=1,j=1}^{l,m} \delta_{ij} \quad \text{(Equation 6)}$$

If all resonators respond in exactly identical ways, $\delta_{ij}=\delta_0$, the formula for the array signal reduces to that of an individual resonator:

$$V_{arr} = \frac{V_b}{2lm} \sum_{i=1,j=1}^{l,m} \delta_{ij} = \frac{1}{2} V_b \delta_0 \quad \text{(Equation 7)}$$

The addition of such signals with random phase is equivalent to a random walk in the complex plane, which implies that the expected magnitude of the sum will scale as the square root of the total number of terms in the sum:

$$\langle V_{arr} \rangle = \frac{1}{2} V_b \frac{\sqrt{N}}{N} \delta_0 = \frac{1}{2\sqrt{N}} V_b \delta_0 \quad \text{(Equation 8)}$$

Since the bias signal $V_b$ normally scales as $\sqrt{N}$, the use of arrays does not offer any advantages with respect to the use of an individual device in this case. It is therefore preferable to keep the drive phase as uniform as possible for all the resonators in the array.

Effect of Frequency Dispersion: Theoretical Framework

The finite resolution of e-beam and optical lithography can introduce slight variations in the dimensions of the fabricated resonators. As a result, all resonators in the array can have slightly different mechanical properties, and in particular different resonance frequencies. One way to judge whether this dispersion in resonance frequency is significant is by comparing it to the natural width of the resonance under typical operating conditions. For example, nanoscale resonators shown in FIG. 2B have a typical quality factor on the order of 100 in air at atmospheric pressure, corresponding to a resonance width that is 1% of the resonance frequency. Therefore, if the dispersion of resonance frequency is smaller than 1%, the individual resonance curves will strongly overlap and the Lorentzian-response term of individual resonators may be treated as the same, leading to the summed array response being Lorentzian as well. In this case, the maximum possible amplitude of the array response can be obtained. Conversely, if the dispersion of the frequencies is much larger than 1%, the sum of the individual Lorentzian response curves will be much broader than an individual resonance, and the peak array signal will be much reduced with respect to the maximum possible signal.

To quantify this qualitative description, we consider the problem of adding up many Lorentzian resonance curves with randomly distributed resonance frequencies. The normal or Gaussian probability distribution is a common choice in such simulations; however, in reality the probability of finding resonance frequencies far off the mean is much larger than would be expected in a Gaussian distribution.

To model this large number of outliers, it is more appropriate and convenient to use the Cauchy distribution, which has the probability density function similar to the Lorentzian:

$$p(\omega_R) = \frac{Q_{distr}/2\pi\omega_0}{1+\left(\frac{\omega_R-\omega_0}{2\omega_0/Q_{distr}}\right)^2} \quad \text{(Equation 9)}$$

where $\omega_0$ is the center frequency of the distribution and $Q_{distr}$ characterizes the width of the distribution, similar to the way that a quality factor characterizes the width of a Lorentzian curve. The Cauchy distribution more accurately describes the long tails of the frequency distribution that we observe in practice and has the added advantage that the expected form of the array response can be calculated analytically, as shown below.

Figure 10A:
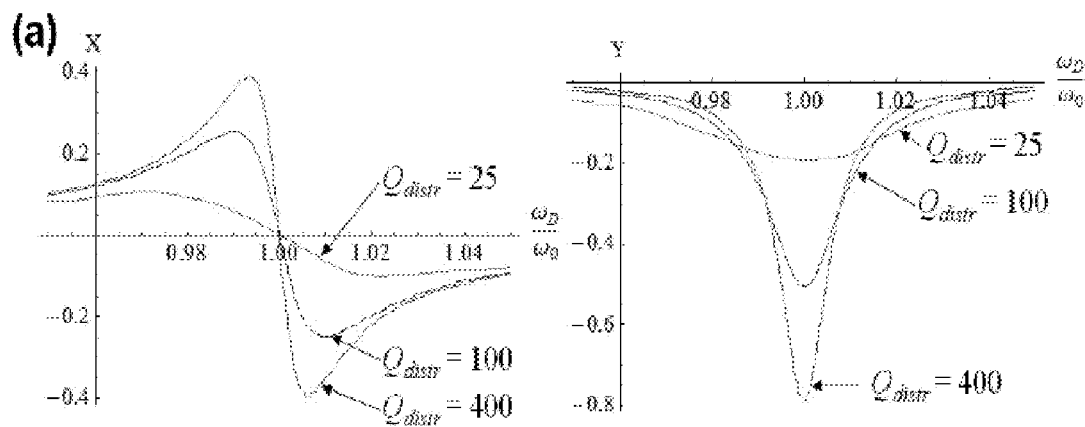
FIG. 10A shows a simulated response of 2800 cantilevers with Q=100 and $Q_{dist}$ of 400, 100, and 25. The effective quality factors $Q_{eff}$ are ≈80, 50, and 20, respectively.
Figure 10B:
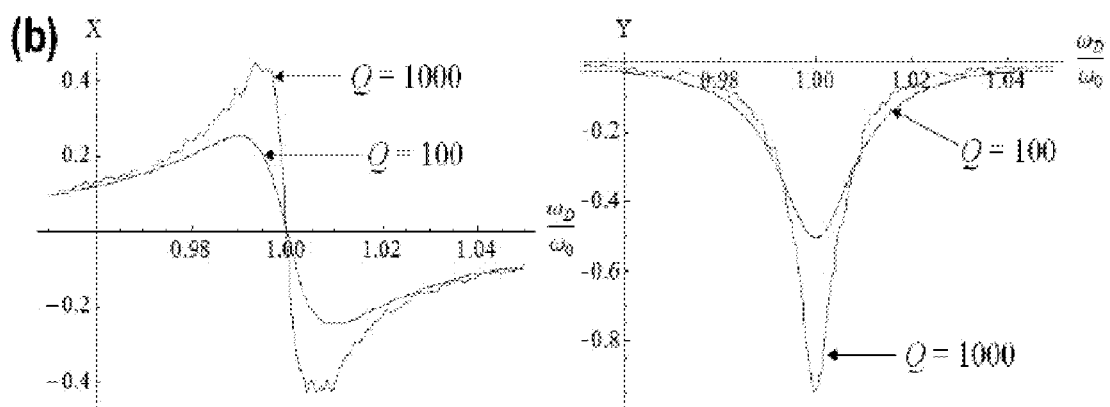
FIG. 10B shows a simulated response of 2800 cantilevers with $Q_{dist}$ of 100 and 1000, which approximately corresponds to the frequency dispersion and quality factors in air and vacuum of actual arrays used in experiments.

To illustrate this effect of the resonance frequency dispersion on the shape of the array response, we have performed numerical simulations for an array consisting of 2800 elements (FIG. 10A-B)

The response of a forced, damped harmonic oscillator is given by $$s(\omega_D) = A \frac{\omega_R^2/Q}{\omega_R^2 - \omega_D^2 + i\omega_R\omega_D/Q} \quad \text{(Equation 10)}$$

where A is the amplitude of the resonance signal, $\omega_R$ is the resonance frequency, Q is its quality factor, and $\omega_D$ is the frequency of the drive. If the quality factor of an individual resonator is large, Q>>1, the response near the resonance can be approximated by the complex Lorentzian $$s(\omega_D) = A \frac{\omega_R/Q}{\omega_R - \omega_D + i\omega_R/(2Q)}. \quad \text{(Equation 11)}$$

The expected signal from one array cantilever with a randomly distributed resonance frequency is then a convolution of the complex Lorentzian response with the Cauchy distribution:

$$\langle s(\omega)\rangle \approx \int_{-\infty}^{\infty} \frac{\omega_R/Q}{\omega_R - \omega_D + \frac{i\omega_R}{2Q}} \times \frac{Q_{disrt}/2\pi\omega_0}{1 + \left(\frac{\omega_R - \omega_0}{2\omega_0/Q_{distr}}\right)^2} d\omega_R = \frac{A\omega_0/2Q}{\omega_0 - \omega_D + \frac{i\omega_R}{2}\left(\frac{1}{Q_{distr}} + \frac{1}{Q}\right)}$$

(Equation 12)
which is simply the complex Lorentzian response with a new effective quality factor $Q_{eff}=1/(Q^{-1}+Q_{distr}^{-1})$ and a new effective amplitude $A_{eff}=AQ_{eff}/Q$. The expected signal of the entire array will have the same form, since it is essentially the sum of the expected signals of individual cantilevers and we assume all cantilevers in the array to be described by the same Cauchy probability distribution. In addition, for a large array, N>>1, the typical response generally will not deviate far from the expected response as the random variations introduced by individual resonances will largely average out. Therefore, the frequency dispersion effectively has the same result as an additional source of damping, corresponding to a quality factor $Q_{distr}$, which reduces the effective quality factor of the array from Q to $Q_{eff}=1/(Q^{-1}+Q_{distr}^{-1})$.

Array Functionalization

Resonators in an array can be adapted for detection of specific analytes. Resonators are functionalized by coating the resonators with a coating material capable of absorbing, adsorbing, or otherwise interacting with a target analyte. The analytes that can be detected are not limited. For example, the resonators can be adapted to detect, for example, mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, a toxin, or combinations thereof. The physical state of the analyte is not limited. The analyte can be, for example, a solid, a liquid, a gas, or a plasma.

A coating material is applied to at least a portion of one or more resonators of an array. For example, the coating material may be applied to the topside or bottom side of one or more resonators or to portions thereof. Coating materials may be, for example, an epoxy resin such as Novolac™, a fluoropolymer such as FluoroPel™, a silicon polymer, a gold layer, a palladium layer, an alcohol-absorbent polymer, a water-absorbent material, a chemical-sensitive polymer, a chemical-sensitive layer, a biosensitive material, a thiol, or combinations thereof.

In one embodiment, resonators can be coated with a polymer capable of binding a specific analyte. In one embodiment, the resonators are coated with a silicon film polymer. In one embodiment, the silicon film coating is 10 nm to 20 nm thick.

Various application methods can be used to deposit or apply coating materials and to treat surfaces of the resonators. Coating materials comprise, for example, a dipped coating, a sprayed coating, a masked coating or a dispensed coating disposed on at least a portion of one or more resonators. Coating materials can, for example, be grown chemically on the resonator surface or deposited through thin-film deposition techniques such as evaporation, sputtering, or chemical vapor deposition.

In one embodiment, each array is functionalized for detection of a single analyte. In one embodiment, at least 50%, at least 75%, or at least 90% of the resonators in an array are functionalized for the detection of a single analyte. In one embodiment, all resonators in an array are functionalized for detection of a single analyte. In one embodiment, multiple arrays are functionalized for detection of a single analyte. In one embodiment, a sensor comprises multiple arrays, and each array is functionalized for detection of a different analyte. In one embodiment, a sensor comprises multiple arrays, and each array is independently functionalized for the detection of an analyte, and arrays may or may not be functionalized for detection of the same analyte as other arrays.

Analyte Delivery System

Target analytes, which may be located in a liquid or gas carrier such as air or water, in a low-pressure gas, or a plasma, may be delivered in a forced or free manner towards the resonators where they contact the surface of the resonator probes and invoke shifts in resonant frequency, Q factor, impedance, or deflection amplitudes.

A suitable analyte delivery system can comprise any mechanism of exposing the resonators to an analyte. For example, the delivery system can comprise a pump or a fan. The delivery system can comprise a chamber with a valve, wherein the valve can be opened and closed. The delivery system can comprise a purification device, such as a chromatography column (FIG. 9). In one embodiment, the purification device is a gas chromatography column.

Analyte Sensing

One or more functionalized resonators can be adapted to respond when exposed to a target analyte. Functionalized resonators may respond by absorbing, adsorbing, or otherwise interacting with the target analyte. When exposed to the target analyte, functionalized resonators may increase or decrease in mass, or become more rigid or less rigid.

In one embodiment, a method of sensing an analyte comprises exciting resonators into vibration at a resonance frequency and detecting the vibration. In one embodiment, the resonators are a part of an array, wherein the resonators in the array are adapted to vibrate at about the same resonance frequency and about the same phase, wherein the resonators are arranged in a plurality of rows and a plurality of columns, wherein at least one array is electrically connected to an actuator and a signal detector, and wherein at least one resonator is functionalized for detection of at least one analyte.

In one embodiment, a method of sensing an analyte can utilize the resonators, arrays, articles, or analytes described herein.

In one embodiment, the presence of an analyte is detected by measuring shifts in resonant frequency, Q factor, impedance, or deflection amplitudes upon exposing the resonators to an analyte.

If the drive and bias frequencies remain constant and the central peak frequency of the arrays $\omega_R$ changes by $\Delta\omega_R$ due to an absorbed mass $\Delta m$, the dispersive components of the resonance voltage signal will change by $$\Delta Y \approx \frac{dY}{d\omega_R}\Delta\omega_R \approx \frac{2Q_{eff}A_{arr}}{\omega_R}\Delta\omega_R \approx \frac{Q_{eff}A_{arr}}{m_c}\Delta m \quad \text{(Equation 13)}$$

where $A_{arr}$ is the voltage amplitude of the array resonance peak, and $m_c$ is the mass of the resonator. Therefore, as long as the total frequency shift is smaller than the resonance width, we can easily infer the changes in the resonance frequency from the measured changes in the dispersive quadrature of the signal.

In one embodiment, the sensor can detect an analyte present at ppm or higher concentrations. In one embodiment, the present invention can detect an analyte at ppb or higher concentrations.

One advantage of the present invention is the ability to detect a low concentration of analyte at short exposure times. For example, in one embodiment, analyte can be detected at ppm concentrations with a few second analyte exposure time. For example, the exposure time can be less than about 10 seconds, less than about 5 seconds, less than about 3 seconds, less than about 2 seconds, or less than about 1 second. In one embodiment, the exposure time is more than about 5 seconds.

In one embodiment, analyte can be detected at ppb concentrations with a few second analyte exposure time. In one embodiment, analyte can be detected at ppb concentrations with an exposure time that is two seconds or less.

In one embodiment, the sensor comprises multiple arrays, and each array is adapted to sense a different analyte.

In one embodiment, the resonator vibration is detected before, during, and/or after exposing the resonators to the analyte. In one embodiment, the method comprises exposing an article to an analyte and detecting a shift in the resonance frequency of an array resulting from exposure to the analyte. In one embodiment, the frequency shift can be due to the interaction between the analyte and one or more functionalized resonators.

NEMS Array Fabrication

The present invention is also directed to a method of fabricating NEMS or MEMS resonator array sensors. The NEMS or MEMS resonator array sensors may be made by any suitable method. A non-limiting example of sensor fabrication is described in the working examples section of this application.

WORKING EXAMPLES

Example 1

Array Fabrication

NEMS arrays were fabricated from CMOS-compatible materials using state-of-the-art microelectronic lithography and etching techniques with nanoscale alignment. The high-frequency (HF) NEMS arrays were fabricated from a 200-mm SOI wafer with 160-nm-thick silicon layer (resistivity≈10 Ω·cm) and 400-nm-thick buried oxide layer (FIG. 1A). An AlSi metal film was deposited by sputtering technique at 175° C. The metal film is further described in Andreucci et al. (WO 2011/006885). Its thickness varied between 45 and 70 nm depending on the design. Optical deep ultraviolet (248 nm wavelength) lithography was then used to pattern the thin-film metal features: wirebonding pads, leadframe, and the NEMS array itself. We were able to achieve a better than 200-nm resolution in a reproducible way using a positive resist and a bottom anti-reflective coating (BARC).

The exposed areas of the metal film were etched using reactive ion etching (RIE) in boron trichloride ($BCl_3$) and argon (Ar) plasma. The resulting metallization layer served as a mask for the subsequent $CF_4$ plasma etching of the 160-nm-thick silicon structural layer down to the buried oxide. In some designs, additional lithography steps were performed to define bare-silicon (metallization-free) areas on beams or resonators before the final silicon etching. In this case, the accuracy of alignment between the lithography levels was better than 30 nm. In some designs, the metal layer on the bonding pads and lead-frames was thickened to 650 nm to facilitate the wirebonding procedure, decrease the access resistance, and improve the impedance matching.

Finally, the NEMS resonators or beams were suspended using an analyte HF etch step that was carefully timed to minimize the undercut of the anchors. The arrays were typically etched for 6 hours at 32° C. in HF analyte concentration of approximately 10%, resulting in silicon dioxide etching rate of 1.2 nm/min. The analyte HF did not significantly attack the metal layer, with the etch rate being only 1 nm/hour.

With this process, the first 200-mm wafers of NEMS VLSI were produced, each containing more than 3.5 million NEMS. Some arrays produced by the above method contained 2,800 NEMS resonators and occupied an area 0.14 mm by 1.0 mm. Other arrays contained up to 6,800 NEMS resonators and occupied an area of 0.2 mm by 0.6 mm, achieving an integration density of approximately 60,000 NEMS/$mm^2$, and a functional device yield of approximately 95%.

Example 2

Frequency Dispersion

Figure 6B:
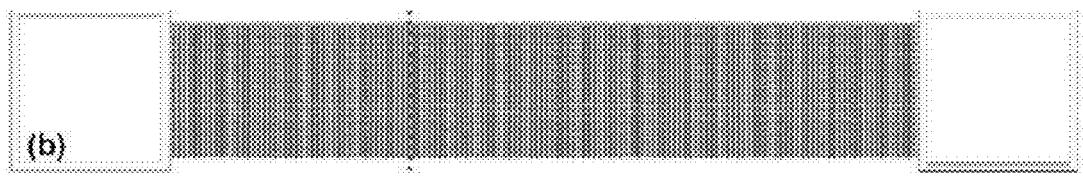
FIG. 6B is a top-view schematic of a 140×20 array of cantilevers. The dotted line shows the positions of the laser spot used to acquire the optical spectra of FIG. 6A.

To further study the dispersion of frequencies in the arrays, measurements were also done using thermoelastic actuation and optical detection in vacuum. The optical detection setup was a simple reflection interferometer with a spot size of approximately 10 μm, as described in Masmanidis et. al., Science 2007 317, 780-783. The results are shown in FIG. 6A, where we plot the interferometer signal of an array of 2.8-μm-long, 1.2-μm-wide resonators versus excitation frequency and the position of the beam spot. The position of the beam spot was stepped every 5 μm across the width of an array (see FIG. 6B).

The small size of the optical spot allowed us to detect only about a dozen resonators within the beam spot instead of the entire array of 2,800 resonators. The majority of individual resonances were situated near the central frequency of 18.6 MHz, and these resonances formed the main peak of the array response. Similar to electrical data on other arrays, however, there were also a number of "outliers", especially at frequencies above the central peak. Some of these resonances were sufficiently well resolved to be fitted individually. The quality factor of such individual resonances in vacuum was approximately 1,100.

Example 3

Combined Series-Parallel Configuration

Figure 3A:
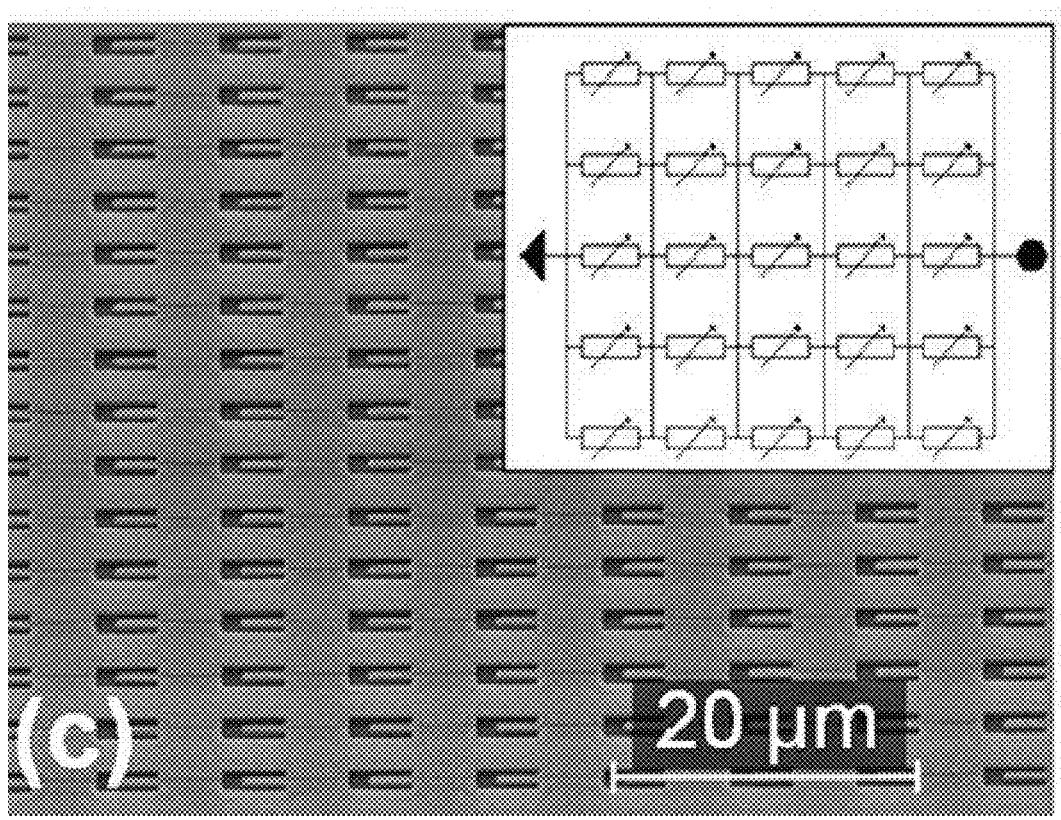
FIG. 3A is a scanning electron micrograph of a section of a resonator array. The inset is a schematic of a combined series-parallel electrical connection of array elements.
Figure 3B:
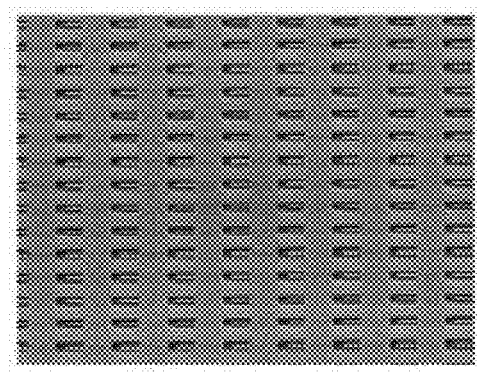
FIG. 3B is a scanning electron micrograph of a section of a resonator array.
Figure 3C:
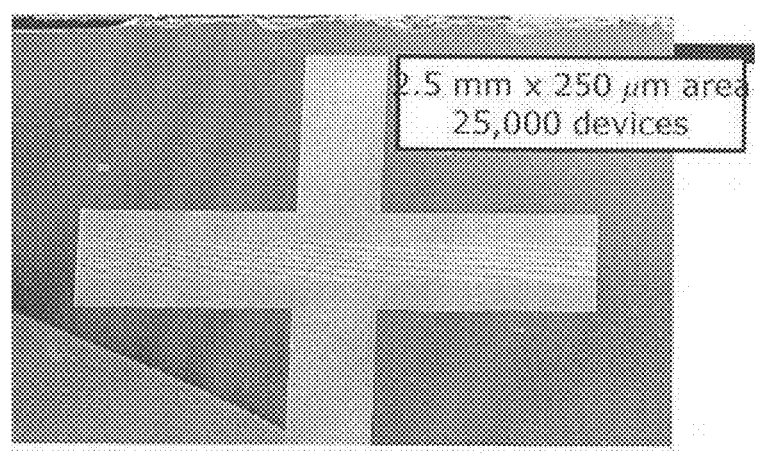
FIG. 3C is a scanning electron micrograph of a 2.5 mm×250 μm array composed of 25,000 resonators.
Figure 3D:
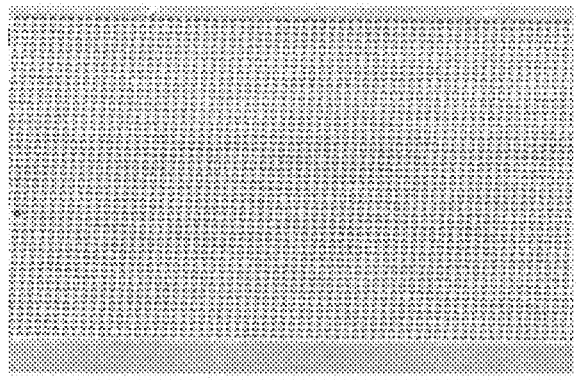
FIG. 3D is a scanning electron micrograph of a section of a 2.5 mm×250 μm array composed of 25,000 resonators.
Figure 3E:
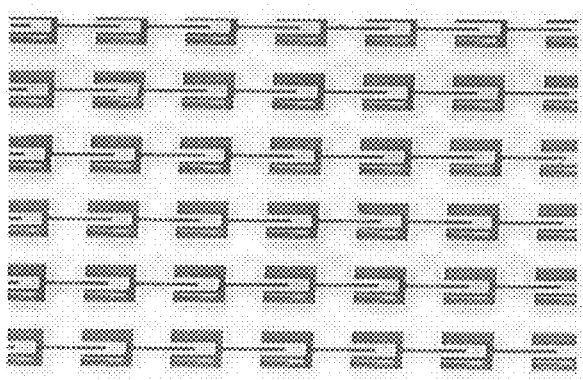
FIG. 3E is a zoomed-in view of a scanning electron micrograph of a section of a 2.5 mm×250 μm array composed of 25,000 resonators.
Figure 3F:
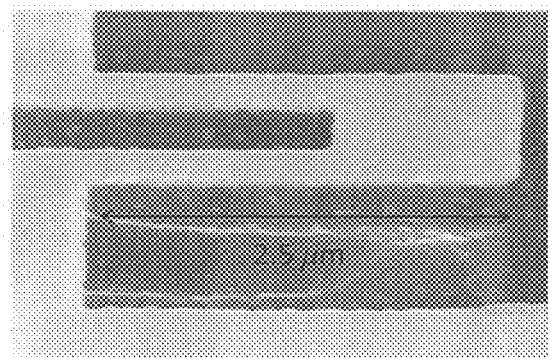
FIG. 3F is a scanning electron micrograph of a single resonator of an array.
Figure 3G:
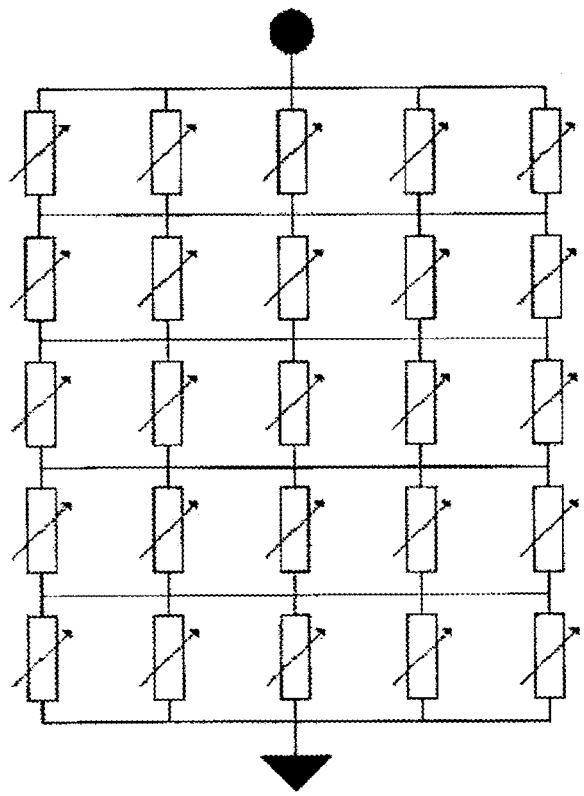
FIG. 3G is a schematic of a combined series-parallel electrical connection of rows and columns of array elements in which all resonators of a row are connected in parallel and all resonators of a column are connected in series.

A straightforward approach to harnessing the power of many individual NEMS in large-area arrays is to connect them electrically in a combined series-parallel configuration, shown in FIG. 3D. A single-port (signal and ground) connection to the array was made through electrodes on opposite edges of the array. The individual NEMS were excited into vibration using electrothermally-generated strain, which allowed us to actuate each array element with essentially identical driving phases.

The resulting motion was detected electrically through the metal surface layer's piezoresistive response. The motion of the array resonators was actuated thermoelastically and detected piezoresistively using the two-port downmixing measurement scheme described above. In the two-port scheme, a single metal loop was used for both thermoelastic actuation and piezoresistive detection. This measurement scheme worked in the same way for arrays as for individual resonators, the only difference being the need to supply more RF power. To further maximize the resonance signal visibility, we measured two arrays at the same time using a balanced differential scheme.

Resonance response was measured in a vacuum and in air using two arrays with cantilevers of nominal lengths of 2.0 and 2.1 micrometers. Resonance peaks corresponding to the two cantilevers are plotted in FIG. 7A-B, with the lower-frequency peak corresponding to the array with longer cantilevers and vice versa.

The vacuum response curves (FIG. 7A) featured many sharp features caused by the individual resonances of cantilevers whose frequency lied outside the majority of resonance peaks of the array. These features were reproducible and larger than the amplitude of measurement noise by approximately two orders of magnitude. According to theory, the individual resonances should be smaller than the overall peak by a factor of $N \times Q_{eff}/Q \approx 2800*100/1000=280$. However, we found the sharp features to be approximately 100 times smaller than the overall peak, suggesting that they are not individual resonances, but rather superpositions of several resonances. In air, these variations were smoothed out, as shown in FIG. 7B, because much more RF power was applied to drive and detect the resonances in air. The amount of RF power used varied between 0.1 W to 1.0 W.

Example 4

Functionalization and Analyte Sensing

In to the present example, an array was operated in ambient air, and an analyte was delivered using a 90-cm-long gas-chromatography column positioned approximately 100-200 micrometers above the sensor array (FIG. 9). The resonators of the array were coated with the polymer DKAP, a silicone copolymer developed at Sandia National Laboratory for detection of phosphonate gas molecules that are precursors and simulants of nerve gas agents. A droplet of DKAP solution was put on the array chip surface and left to dry in air, leaving a thin (10-20 nm) film of polymer on the array resonators.

Functionalization of the array did not have a measurable effect on the frequency or the effective quality factor of the array response. However, the quality factor was noticeably affected by the flow of the hydrogen carrier gas through the column. When the GC system was in operation, the hydrogen carrier gas was forced out of the bottom end of the column at the rate of 1-2 sccm (standard cubic centimeters per minute) and largely displaced the air in the immediate vicinity of the array. Because the viscosity of hydrogen is lower than that of air, this increased the quality factor of individual resonances, Q, and therefore the effective quality factor of the entire array in accordance with the formula $Q_{eff}=1/(Q^{-1}+Q_{distr}^{-1})$. In practice, the effective quality factor typically increased from approximately 50 to approximately 60.

Solutions of diisopropyl methylphosphonate (DIMP), a nerve gas simulant, in $CS_2$ solvent were injected into a gas chromatography column system, and open loop measurements of frequency shift of the array sensor were performed. The open-loop frequency measurements of frequency shift were carried out by monitoring the dispersive quadrature of the Lorentzian response (see, for example, curve Y in FIG. 7B).

Figure 8:
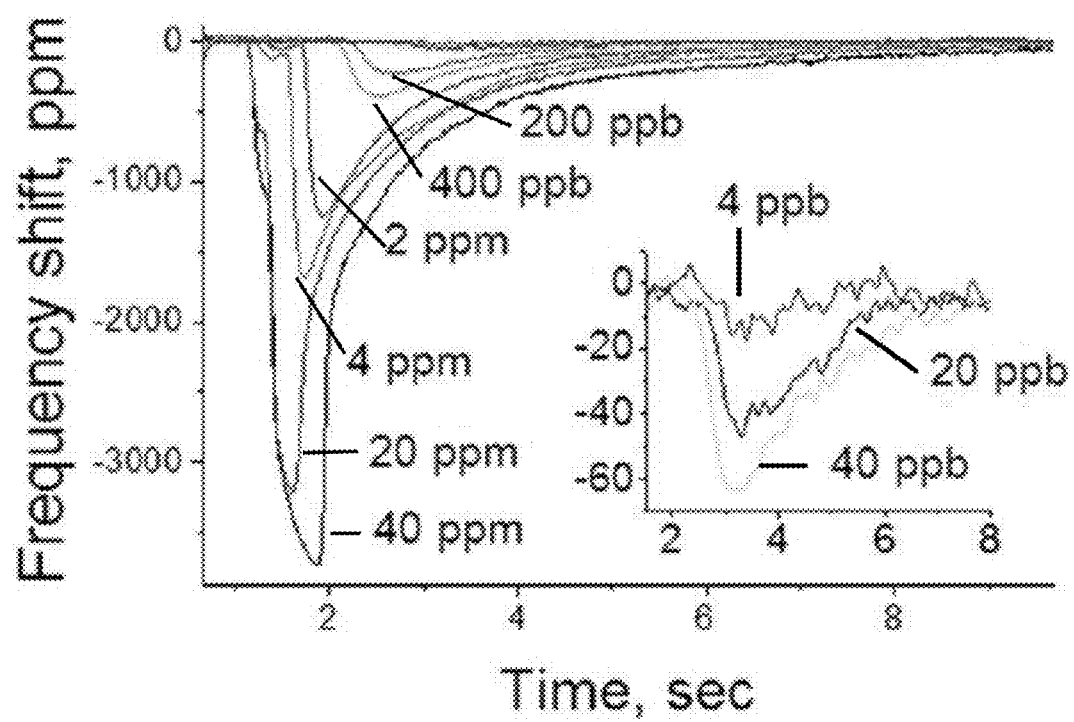
FIG. 8 is a gas chromatogram showing a concentration sensitivity of 1.2 ppb.

FIG. 8 shows the resulting chromatograms for a wide range of DIMP mass injections. The downward shift in the frequency response of the array was caused by the uptake of DIMP molecules by the DKAP polymer that covered the resonators as the chemical was eluted from the open end of the GC column. The total observed frequency shift did not exceed $0.4\% \ll 1/Q_{eff} \approx 2\%$, ensuring a linear relationship between the measured dispersive component and the loading mass.

The resulting average concentrations c in the eluted peaks are calculated as $c=(c_l \cdot V_l \cdot V_m \cdot S_R)/(MW \cdot F \cdot \Delta t)$, where $c_l$ is the mass density of DIMP in the liquid sample, $V_l$ is the liquid volume of sample injected into the column, $V_m$=22.4 liter/mol is the molar volume of an ideal gas at ambient temperature and pressure, $S_R$ is the injection split ratio, MW is the molecular weight of the analyte, $\Delta t$ is the peak width in time, and F is the column flow rate.

At large concentrations (above 1 ppm), the frequency shift peak area did not follow a linear relationship with the concentration of DIMP due to saturation of the polymer film. The response was more linear at smaller concentrations, with both the shape and the delay of the peak independent of the DIMP concentration (see inset to FIG. 8). The data demonstrate a minimum detectable concentration of approximately 1.2 ppb in a 1-Hz bandwidth, which is roughly optimal for detecting short-column pulses a few seconds in length.

Example 5

Simulations

Simulations were performed in which all resonators were assumed to have a quality factor of 100, corresponding to the experimental value in air. The width of the Cauchy distribution was varied, starting from a distribution width much smaller than the natural width of the resonance, $Q_{distr} \gg Q$, and ending with a distribution width much larger than the natural width of the resonance, $Q_{distr} \ll Q$. As expected, increasing the width of the frequency distribution broadened the resonance peak of the entire array and reduced its amplitude.

As shown in FIG. 10A, the simulated response curves did not deviate significantly from the perfect Lorentzian curves due to the large number of elements in the array and their relatively low quality factors. However, the fact that the overall response curves of the array consist of many narrow lines corresponding to individual resonators became evident when the quality factors of individual resonances were high enough, as shown in FIG. 10B. These curves simulated the response of actual arrays used in experiments in air and vacuum. The frequency distribution width of the typical arrays were on the order of 1%, corresponding to $Q_{distr}=100$, and the quality factors of individual resonances were on the order of 100 and 1000 in air and vacuum, respectively. As a result, the experimental curves in vacuum had more "fine structure" than those in air due to the response of individual cantilevers.

The differences between different resonators in the array are, of course, not limited to the variations in the drive phase and resonance frequencies. The quality factors and the amplitudes of response of individual resonators will also vary. However, these variations are relatively insignificant and have a negligible effect on the overall response of the arrays.

What is claimed is:

1. An article comprising:
at least one array comprising a plurality of resonators, wherein the resonators are arranged in a plurality of rows and a plurality of columns,
and wherein the resonators are adapted to vibrate at about the same resonance frequency and about the same phase, wherein the article is configured to detect at least one analyte based on contact of the analyte with the surface of the resonators.

2. The article of claim 1, wherein the resonators are cantilevers.

3. The article of claim 1, wherein the resonators are nanoresonators.

4. The article of claim 1, wherein the resonators comprise piezoresistors.

5. The article of claim 1, wherein the array comprises at least 1,000 resonators.

6. The article of claim 1, wherein the array comprises at least 25,000 resonators.

7. The article of claim 1, wherein the array comprises at least 100,000 resonators.

8. The article of claim 1, wherein the resonators in the array are substantially identical.

9. The article of claim 1, wherein the resonators are about 1.6 micrometers to about 5 micrometers long, and wherein the resonators are about 800 nanometers to about 1.2 micrometers wide.

10. The article of claim 1, wherein the resonators are adapted to vibrate independently.

11. The article of claim 1, wherein the resonators are electrically coupled using a combined series-parallel configuration.

12. The article of claim 1, wherein the resonators are electrically coupled using a combined series-parallel configuration, and wherein at least one row of resonators is connected in parallel, and wherein at least one column of resonators is connected in series.

13. The article of claim 1, wherein the resonators are electrically coupled using a combined series-parallel configuration, and wherein all resonators of a row are connected in parallel and all resonators of a column are connected in series.

14. The article of claim 1, further comprising an actuator and a signal detector electrically connected to the array.

15. The article of claim 1, further comprising an actuator and a signal detector electrically connected to the array, wherein the resonators are adapted to vibrate independently and wherein the resonators are adapted so that signals based on the resonator vibration are electrically coupled.

16. The article of claim 1, further comprising an actuator and a signal detector electrically connected to the array, wherein the actuator is adapted to excite the resonators into vibration at a resonance frequency by electric actuation.

17. The article of claim 1, further comprising an actuator and a signal detector electrically connected to the array, wherein the actuator is adapted to excite the resonators into vibration at a resonance frequency by thermoelastic actuation.

18. The article of claim 1, further comprising an actuator and a signal detector electrically connected to the array, wherein the signal detector is a piezoresistive signal detector.

19. The article of claim 1, further comprising an actuator and a signal detector electrically connected to the array, wherein at least one metal loop is used for both actuation and signal detection.

20. The article of claim 1, further comprising an actuator and a signal detector electrically connected to the array, wherein the article comprises multiple arrays that can be measured at the same time.

21. The article of claim 1, further comprising an actuator and a signal detector electrically connected to the array, wherein the article comprises multiple arrays that can be detected at the same time, wherein the resonators of each array are adapted to resonate at a center frequency, and wherein the resonators of each array are adapted to vibrate at a different center frequency than the resonators of other arrays.

22. The article of claim 1, wherein each resonator has a resistance of about 1 Ω to about 20 Ω.

23. The article of claim 1, wherein each resonator has a resistance of about 7 Ω.

24. The article of claim 1, wherein the plurality of rows and columns is arranged so that the total resistance of the array is about 1 Ω to about 100 Ω.

25. The article of claim 1, wherein the plurality of rows and columns is arranged so that the total resistance of the array is about 50 Ω.

26. The article of claim 1, wherein the array is able to handle power input of at least 900 mW per array.

27. The article of claim 1, further comprising an analyte delivery system.

28. The article of claim 1, further comprising an analyte delivery system, wherein the analyte delivery system comprises a chamber with a valve, and wherein the array is exposed to an analyte by opening the valve.

29. The article of claim 1, further comprising an analyte delivery system, wherein the analyte delivery system is a gas chromatography column that is connected to the array.

30. The article of claim 1, wherein the resonators are coated with a coating material capable of interacting with at least one analyte.

31. The article of claim 1 comprising multiple arrays, wherein the resonators are coated with a polymer capable of interacting with at least one analyte, and wherein each array is configured to detect a single analyte.

32. The article of claim 1 comprising multiple arrays, wherein the resonators are coated with a polymer capable of interacting with at least one analyte, and wherein each array is configured to interact with at least one analyte, and wherein the article is configured to interact with at least two analytes.

33. The article of claim 1, further comprising an actuator and a signal detector electrically connected to the array, and an analyte delivery system connected to the array, and wherein the resonators are functionalized for detection of at least one analyte, and wherein the article is capable of detecting an analyte present at a parts per billion concentration.

34. The article of claim 1, wherein the resonators are distributed over at least a 100 nm² area.

35. The article of claim 1, wherein the array has a maximum resonator density of between 4 and 6 million resonators per square centimeter.

36. The article of claim 1, wherein the sensor is adapted for a single measurement circuit.

37. The article of claim 1, wherein the resonators are coated with a coating material capable of interacting with at least one analyte, wherein the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

38. An article comprising: at least one array comprising a plurality of resonators, wherein the resonators are arranged in a plurality of rows and a plurality of columns, wherein the resonators are electrically coupled using a combined series-parallel configuration, and wherein all resonators of a row are connected in parallel and all resonators of a column are connected in series, wherein the article is configured to detect at least one analyte based on contact of the analyte with the surface of the resonators.

39. The article of claim 38, wherein the resonators are about the same size and wherein the resonators are adapted to independently vibrate at about the same resonance frequency and about the same phase.

40. An article comprising: at least one array comprising a plurality of resonators wherein the resonators are adapted to sense an analyte present at a part per billion concentration or less, wherein the article is configured to detect at least one analyte based on contact of the analyte with the surface of the resonators.

41. The article of claim 40, wherein the resonators are arrayed in columns and rows.

42. The article of claim 40, wherein the article is adapted for improved signal-to-noise ratios.

43. The article of claim 40, wherein the article is adapted for improved power matching.

44. The article of claim 40, wherein the article is adapted for improved power handling.

45. The article of claim 40, wherein the article is adapted for improved robustness.

46. The article of claim 40, wherein the resonators are arranged in columns and rows and are electrically coupled in a combined series-parallel configuration.

47. The article of claim 40, wherein the resonators are about the same size, and wherein the resonators are adapted to independently vibrate at about the same resonance frequency and about the same phase.

48. The article of claim 40, wherein the resonators are functionalized for detection of at least one analyte.

49. The article of claim 40, wherein the resonators are adapted for measurement by a single circuit.

50. A method comprising:
exciting resonators into vibration at a resonance frequency; and
detecting the vibration;
wherein the resonators are a part an array, wherein the resonators are arranged in a plurality of rows and a plurality of columns;
wherein the resonators in an array are adapted to vibrate at about the same resonance frequency and about the same phase;
wherein at least one array is electrically connected to an actuator and a signal detector; and
wherein at least one resonator is configured to detect at least one analyte, based on contact of the analyte with the surface of the resonator.

51. The method of claim 50, wherein the vibration is detected via a piezoresistor disposed on the resonators.

52. The method of claim 50, further comprising exposing the article to an analyte.

53. The method of claim 50, further comprising exposing the article to an analyte and detecting a shift in the resonance frequency of the array resulting from exposure to the analyte.

54. The method of claim 50, further comprising exposing the article to an analyte and detecting a shift in the resonance frequency of the array resulting from exposure to the analyte, wherein the shift in the resonance frequency is due to an interaction between the functionalized resonator and the analyte.

55. The method of claim 50, further comprising exposing the article to an analyte and sensing of the analyte, wherein the article is exposed to the analyte for a period of two seconds or less.

56. The method of claim 50, further comprising exposing the article to an analyte and sensing of the analyte, wherein the analyte is present at a part per billion concentration or less.

57. The method of claim 50, wherein the resonators are cantilevers.

58. The method of claim 50, wherein the resonators are nanoresonators.

59. The method of claim 50, wherein the resonators are piezoresistors.

60. The method of claim 50, wherein the array comprises at least 1,000 resonators.

61. The method of claim 50, wherein the array comprises at least 25,000 resonators.

62. The method of claim 50, wherein the array comprises at least 100,000 resonators.

63. The method of claim 50, wherein the resonators are substantially identical.

64. The method of claim 50, wherein the resonators are about 1.6 micrometers to about 5 micrometers long.

65. The method of claim 50, wherein the resonators are about 800 nanometers to about 1.2 micrometers wide.

66. The method of claim 50, wherein the resonators are electrically coupled using a combined series-parallel configuration.

67. The method of claim 50, wherein the resonators are electrically coupled using a combined series-parallel configuration, wherein all resonators of a row are connected in parallel and all resonators of a column are connected in series.

68. The method of claim 50, wherein the resonators are adapted to vibrate at about 15 MHz to about 30 MHz.

69. The method of claim 50, wherein the resonators are adapted to vibrate independently.

70. The method of claim 50, wherein the resonators are adapted to vibrate independently and wherein signals based on the resonator vibration are electrically coupled.

71. The method of claim 50, wherein the resonators are excited into vibration by electric actuation.

72. The method of claim 50, wherein the resonators are excited into vibration by thermoelastic actuation.

73. The method of claim 50, wherein the signal is detected by a two-port downmixing measurement scheme.

74. The method of claim 50, wherein at least one metal loop is used for actuation and signal detection.

75. The method of claim 50, wherein the article comprises multiple arrays that can be measured at the same time.

76. The method of claim 50, wherein the article comprises multiple arrays that can be detected at the same time, wherein each array resonates at a center frequency, and wherein the article resonates at at least two center frequencies.

77. The method of claim 50, wherein each resonator has a resistance of about 1Ω to about 20 Ω.

78. The method of claim 50, wherein the plurality of rows and columns is arranged so that the total resistance of the array is about 1Ω to about 100 Ω.

79. The method of claim 50, wherein the array is able to handle power input of at least 2 watts per array.

80. The method of claim 50, wherein the array is able to handle power input of at least 900 mW per array.

81. The method of claim 50, wherein the resonators are coated with a polymer capable of interacting with at least one analyte.

82. The method of claim 50, wherein the article comprises multiple arrays, wherein the resonators are coated with a polymer capable of interacting with at least one analyte, and wherein each array is configured to detect a single analyte.

83. The method of claim 50, wherein the article comprises multiple arrays, wherein the resonators are coated with a polymer capable of interacting with an analyte, and wherein the article is configured to detect a single analyte.

84. The method of claim 50, wherein the article comprises multiple arrays, wherein the resonators are coated with a polymer capable of interacting with at least one analyte, and wherein each array is designed to interact with at least one analyte, and wherein the article is configured to interact with at least two analytes.

85. The method of claim 50, wherein the resonators are distributed over an at least 100 nm² area.

86. The method of claim 50, wherein the array has a maximum resonator density of between 4 to 6 million resonators per square centimeter.

87. The method of claim 50, wherein the at least one array is connected in a single circuit.

88. The method of claim 50, wherein the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

89. An article comprising:
   at least one array comprising a plurality of resonators,
   wherein the resonators are arranged in a plurality of rows and a plurality of columns,
   wherein the resonators are electrically coupled using a combined series-parallel configuration,
   wherein all resonators of a row are connected in parallel and all resonators of a column are connected in series, and
   wherein the resonators are adapted to vibrate independently at about the same resonance frequency and about the same phase;
   further comprising an actuator and a signal detector electrically connected to the array, wherein the actuator is configured to excite the resonators by electric actuation, and wherein the detector is a piezoresistive detector;
   further comprising an analyte delivery system; and
   wherein the article is configured to detect at least one analyte, based on contact of the analyte with the surface of the resonators.

90. The article of claim 89, wherein the analyte is mercury, hydrogen, an alcohol, water vapor, an explosive material, a chemical element, a chemical compound, an organic material, an inorganic material, a gaseous substance, a liquid, a biological material, a protein, a nucleic acid, a virus, a DNA strand, a bioactive agent, or a toxin.

91. An article comprising:
   at least one array comprising a plurality of resonators,
   wherein the resonators are arranged in a plurality of rows and a plurality of columns,
   and wherein the resonators are adapted to vibrate at about the same resonance frequency and about the same phase,
   further comprising an actuator and a signal detector electrically connected to the array, wherein at least one metal loop is used for both actuation and signal detection.

92. The article of claim 91, wherein the metal loop comprises nichrome, constantan or manganine metal.

93. An article comprising:
   at least one array comprising a plurality of resonators,
   wherein the resonators are arranged in a plurality of rows and a plurality of columns,
   and wherein the resonators are adapted to vibrate at about the same resonance frequency and about the same phase,
   further comprising an actuator and a signal detector electrically connected to the array, wherein the article comprises multiple arrays that can be detected at the same time, wherein the resonators of each array are adapted to resonate at a center frequency, and wherein the resonators of each array are adapted to vibrate at a different center frequency than the resonators of other arrays.

94. A method comprising:
   exciting resonators into vibration at a resonance frequency; and
   detecting the vibration;
   wherein the resonators are a part an array, wherein the resonators are arranged in a plurality of rows and a plurality of columns;
   wherein the resonators in an array are adapted to vibrate at about the same resonance frequency and about the same phase;
   wherein at least one array is electrically connected to an actuator and a signal detector; and
   wherein at least one resonator is configured to detect of at least one analyte, wherein the signal is detected by a two-port downmixing measurement scheme.

95. A method comprising:
   exciting resonators into vibration at a resonance frequency; and
   detecting the vibration;
   wherein the resonators are a part an array, wherein the resonators are arranged in a plurality of rows and a plurality of columns;
   wherein the resonators in an array are adapted to vibrate at about the same resonance frequency and about the same phase;
   wherein at least one array is electrically connected to an actuator and a signal detector; and
   wherein at least one resonator is configured to detect at least one analyte,
   wherein at least one metal loop is used for actuation and signal detection.

96. The method of claim 95, wherein the metal loop is made of nichrome, constantan or manganine metal.

97. A method comprising:
   exciting resonators into vibration at a resonance frequency; and
   detecting the vibration;
   wherein the resonators are a part an array, wherein the resonators are arranged in a plurality of rows and a plurality of columns;

wherein the resonators in an array are adapted to vibrate at about the same resonance frequency and about the same phase;

wherein at least one array is electrically connected to an actuator and a signal detector; and wherein at least one resonator is functionalized for detection of at least one analyte, wherein the article comprises multiple arrays that can be detected at the same time, wherein each array resonates at a center frequency, and wherein the article resonates at at least two center frequencies.

* * * * *